(12) United States Patent
Yerramilli et al.

(10) Patent No.: US 9,970,927 B2
(45) Date of Patent: *May 15, 2018

(54) METHODS FOR DETECTING SYMMETRICAL DIMETHYLARGININE

(71) Applicant: IDEXX Laboratories, Inc., Westbrook, ME (US)

(72) Inventors: Murthy V. S. N. Yerramilli, Falmouth, ME (US); Mahalakshmi Yerramilli, Falmouth, ME (US); Michael Atkinson, Gorham, ME (US); Kwok Kam Yeung, Falmouth, ME (US)

(73) Assignee: IDEXX Laboratories, Inc., Westbrook, ME (US)

(*) Notice: Subject to any disclaimer, the term of this patent is extended or adjusted under 35 U.S.C. 154(b) by 538 days.

This patent is subject to a terminal disclaimer.

(21) Appl. No.: 14/192,956

(22) Filed: Feb. 28, 2014

(65) Prior Publication Data
US 2014/0242723 A1   Aug. 28, 2014

Related U.S. Application Data

(63) Continuation of application No. 13/918,531, filed on Jun. 14, 2013, now Pat. No. 9,091,684, which is a continuation of application No. 12/512,479, filed on Jul. 30, 2009, now Pat. No. 8,481,690.

(60) Provisional application No. 61/086,870, filed on Aug. 7, 2008.

(51) Int. Cl.
*G01N 33/53* (2006.01)
*G01N 33/543* (2006.01)
*C07C 279/12* (2006.01)
*C07K 16/44* (2006.01)
*G01N 33/68* (2006.01)

(52) U.S. Cl.
CPC .......... *G01N 33/53* (2013.01); *C07C 279/12* (2013.01); *C07K 16/44* (2013.01); *G01N 33/54366* (2013.01); *G01N 33/6812* (2013.01)

(58) Field of Classification Search
CPC ...... C07C 279/12; C07K 16/44; G01N 33/53; G01N 33/54366; G01N 33/6812
See application file for complete search history.

(56) References Cited

U.S. PATENT DOCUMENTS

| | | | |
|---|---|---|---|
| 5,726,010 A | 3/1998 | Clark | |
| 6,699,673 B2 | 3/2004 | Aletta | |
| 8,481,690 B2 * | 7/2013 | Murthy | C07C 279/12 435/7.1 |
| 9,091,684 B2 * | 7/2015 | Yerramilli | C07C 279/12 |
| 2006/0094122 A1 | 5/2006 | Boeger et al. | |

FOREIGN PATENT DOCUMENTS

| | | |
|---|---|---|
| EP | 1666884 | 7/2006 |
| WO | 98/49199 | 11/1998 |
| WO | 2002/014873 | 2/2002 |
| WO | 2004046314 | 6/2004 |
| WO | 2006/078813 A2 | 7/2006 |
| WO | 2007074864 | 7/2007 |

OTHER PUBLICATIONS

Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*

Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*

Pravetoni et al., "Structurally distinct nicotine immunogens elicit antibodies with non-overlapping specificities," Biochem. Pharmacol., Feb. 15, 2012; vol. 83, No. 4, pp. 543-550, Published online Nov. 15, 2011.*

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*

Richard, et al., Arginine methylation regulates IL-2 gene expression: a role for protein arginine methyltransferase 5 (PRMT5), Biochem J., 388:379-386 (2005).

Mahler, et al., Identification of a SmD3 epitope with a single symmetrical dimethylation of an arginine residue as a specific target of a subpopulation of anti-Sm antibodies, Arthritis Research & Therapy,7:19-29 (2004).

Brahms, et al., The C-terminal RG Dipeptide Repeats of the Spliceosomal Sm Proteins D1 and D3 contain Symmetrical Dimethylarginines, Which Form a Major B-cell epitope for Anti-Sm Autoantibodies, The Journal of Biological Chemistry, 275:17122-17129 (2000).

Boisvert, et al., Symmetrical dimethylarginine methylation is required for the localization of SMN in Cajal bodies and pre-mRNA splicing, The Journal of Cell Biology, 159:957-969 (2002).

Boisvert, Francois-Michel, A role for arginine methylation in DNA repair, Dissertation abstracts International, 68:34 (2005).

(Continued)

*Primary Examiner* — Galina Yakovleva
(74) *Attorney, Agent, or Firm* — McDonnell Boehnen Hulbert & Berghoff LLP

(57) ABSTRACT

Method of detecting Symmetrical dimethyl arginine (SDMA) in biological samples. SDMA analogs for generating anti-SDMA antibodies having little or no cross-reactivity with asymmetrical dimethyl arginine, arginine, and monomethylarginine. The analogs have a protected or free thiol (—SH) group or hydroxyl (—OH) group that allow them to be linked to a suitable conjugation target which can be, for example, a protein containing molecule of a label. The anti-SDMA antibodies can be used in diagnostic immunoassay for the diagnosis of SDMA associated disorders and/or diseases.

75 Claims, 4 Drawing Sheets

(56) References Cited

OTHER PUBLICATIONS

Bode-Böger, et al., Symmetrical dimethylarginine: A New combined Parameter for renal Function and extent of Coronary Artery Disease; Journal of the American Society of Nephrology; 17:1128-1134 (2006).
Schnabel, et al., Asymmetric Dimethylarginine and the Risk of Cardiovascular events and Death in Patients with Coronary Artery Disease—results from the AtheroGene Study, Circulation Research 97:1-7(2005).
Böger, Rainer, Asymmetric dimethylarginine (ADMA): A novel risk marker in cardiovascular medicine and beyond, Annals of Medicine, 38:126-136 (2006).
Schulze, et al., Determination of a reference value for NG, NG-dimethyl-L-arginine in 500 subjects, European Journal of Clinical investigation, 35:622-626 (2005).
Kielstein, et al., Symmetric dimethylarginine (SDMA) as endogenous marker of renal function—a meta-analysis, Nephrol Dial. Transplant, 21:2446-2451 (2006).
Schulze, et al., Determination of asymmetric dimethylarginine (ADMA) using a novel ELISA assay, Clin. Chem. Lab Med. 42:1377-1383 (2004).
ADMA—ELISA, Enzyme Immunoassay for the quantitative Determination of Endogenous Asymmetric Dimethylarginine (ADMA) in Serum or Plasma, (2007).
SDMA—ELISA, Enzyme Immunoassay for the quantitative Determination of Endogenous Symmetric Dimethylarginine (SDMA) in Serum or Plasma, (2008).
Liu, et al., New Procedures for Preparation and Isolation of Conjugates of Proteins and a Synthetic Copolymer of D-Amino Acids and Immunochemical Characterization of Such Conjugates, Biochemistry 18:690 (1979).
Kitagawa, et al., Preparation and characterization of Hetero-bifunctional Cross-linking Reagents for Protein Modificiations, Chem. Pharm. Bull 29:1130-1135 (1981).
Duncan, et al., A New Reagent Which may be Used to Introduce Sulfhydryl Groups into Proteins, and Its use in the Preparation of Conjugates for Immunoassay, Anal. Biochem 132:68-73 (1983).
Palmer, et al., Reduction and Reoxidation of a Critical Disulfide Bond in the Rabbit Antibody Molecule, J. Biol. Chem 238:2393 (1963).
Bedford, et al., Arginine Methylation: An Emerging Regulator of Protein Function, Mol. Cell, 18:263-272 (2005).
Blackwell, et al., Biological variation of asymmetric dimethylarginine and related arginine metabolites and analytical performance goals for their measurement in human plasma, Eur J. Clin Invest 37:364-371 (2007).
Nijveldt, et al., Handling of asymmetrical dimethylarginine and symmetrical dimethylarginine by the rat kidney under basal conditions and during endotoxaemia, Nephrol Dial. Transplant 18:2542-2550 (2003).
Boisvert, et al., A Proteomic Analysis of Arginine-Methylated Protein Complexes, Molecular & Cellular Proteomics, 2:1319-1329 (2003).
Fleck, et al. Serum concentrations of asymmetric (ADMA) and symmetric (SDMA) dimethylarginine in renal failure patients, Kidney International, 59:14-18 (2001).
Biovendor Research and Diagnostic Products: "Enzyme Immunoassay for the Quantitative Determination of Endogenous Symmetric Dimethylarginine (SDMA) in Serum or Plasma", SDMA ELISA, Instructions for use, (2008).
Upstate cell signaling solutions, "Certificate of Analysis for Anti-dimethyl-Arginine, symmetric (SYM11)," rabbit polyclonal IgG; downloaded May 24, 2011 from www.millipore.com.
Upstate cell signaling solutions, "Certificate of Analysis for Anti-dimethyl-Arginine, symmetric (SYM10)," rabbit antiserum; downloaded May 24, 2011 from www.millipore.com.
"SDMA (human) ELISA kit," Enzo Life Sciences, Version 01: Dec. 8, 2009.
Mosegaard, et al., Effects of breed, gender, exercise and white-coat effect on markers of endothelial function in dogs, Research in Veterinary Science, 82:409-418 (2007).
Product Information List retrieved from DLD Diagnostika GmbH—Online in Jan. 25, 2011.

\* cited by examiner

METHODS FOR DETECTING SYMMETRICAL DIMETHYLARGININE

CROSS-REFERENCE TO RELATED APPLICATION

The application is a continuation of U.S. patent application Ser. No. 13/918,531, filed Jun. 14, 2013, which is a continuation of U.S. patent application Ser. No. 12/512,479, filed on Jul. 30, 2009, which claims the benefit of U.S. Provisional Patent Application Ser. No. 61/086,870, filed Aug. 7, 2008, each of which are incorporated by reference herein in their entirety.

BACKGROUND OF THE INVENTION

Field of the Invention

The invention generally relates to the detection of symmetrical dimethylarginine (SDMA). More particularly, the invention relates to analogs that may be used to generate anti-SDMA antibodies, the anti-SDMA antibodies generated using the SDMA analogues, and uses for anti-SDMA antibodies, including diagnostic methods and devices.

Related Art

It is important to be able to measure renal function quickly and accurately. For example, the dosing of drugs must be adapted for patients with renal insufficiency. Thus, making an accurate assessment of renal function is a requirement in clinical medicine. However, the diagnosis of renal insufficiency is hindered by the lack of reliable markers of glomerular filtration rate (GFR) and/or available diagnostic tests. A widely used measurement of GFR is inulin clearance, but this test is cumbersome and expensive, which essentially reduces its utility in clinical practice. This also holds true for radioisotope clearance tests. Therefore, in clinical practice, serum creatinine is typically used to assess renal function.

A major disadvantage associated with measuring serum creatinine, however, is that there is considerable inter-individual variability associated with muscle mass, protein intake, age, and sex. Furthermore, even after a large part of a patient's renal function is lost, serum creatinine levels may remain in a normal range, meaning that serum creatinine is not useful for early detection of renal insufficiency. Moreover, while approximation of GFR by creatinine clearance can be more informative than serum creatinine, obtaining accurate 24 hour timed urine collections are labor-intensive, and may be difficult depending upon the patient population being tested, such as infants, elderly, individuals with urologic abnormalities, or animals. Accordingly, there is a need for alternative diagnostic markers and methods for testing for renal function.

Symmetrical dimethylarginine (SDMA) is the structural isomer of the endogenous nitric oxide synthetase (NOS) inhibitor asymmetric dimethylarginine (ADMA). Both ADMA and SDMA derive from intranuclear methylation of L-arginine residuals and are released into the cytoplasm after proteolysis. SDMA is produced by protein-arginine methyltransferase 5 (PRMT 5) and PRMT 7. Proteins carrying methylarginines, such as SDMA, monomethylarginine and ADMA, play a role in RNA processing, protein shuttling and signal transduction (Bedford and Richard, Mol. Cell, 2005, April 29, 18(3):263-72). Free SDMA resulting from the degradation of such methylated proteins is mainly eliminated by renal excretion, whereas ADMA is largely metabolized.

ADMA is strongly correlated with risk factors for coronary artery disease (CAD) such as hypertension, hypercholesterolemia, hyperhomocysteinemia, insulin resistance, age, and mean arterial pressure. SDMA is correlated with parameters of renal function, such as glomerular filtration rate (GFR), inulin clearance, and creatinine clearance. SDMA, however may be more than an indicator of renal function. For example, in animals, a high-fat, high-cholesterol diet increases SDMA serum levels without affecting renal function, indicating that SDMA may also be a cardiovascular risk factor. Moreover, anti-SDMA antibodies may also be utilized as a biomarker for systemic lupus erythematosus (SLE). The D1 and D3 proteins of the Sm complex, which has been implicated to play a role in the etiology of SLE, contain C-terminal SDMA.

Accordingly, the inventors have identified a need in the art for a simple, convenient and cost effective method for identifying SDMA in biological samples to assess, for example, renal function, cardiovascular function, and SLE. Also, the inventors have identified the need to provide anti-SDMA antibodies that are specific of SDMA, i.e., that discriminate between molecules that differ only in the methylation state of the two equivalent nitrogens on the guanidino group of SDMA, such as arginine, monomethylarginine, and ADMA.

BRIEF SUMMARY OF THE INVENTION

In one aspect, the invention provides novel SDMA analogs and anti-SDMA antibodies that may be useful in diagnostic immunoassays. The antibodies may have no or substantially no cross-reactivity with arginine, monomethylarginine, and ADMA. In another aspect the antibodies are prepared using an immunogen of the invention. The immunogen includes an SDMA analog conjugated to a carrier protein. In another aspect, the invention is directed to the SDMA analog.

The antibodies of the invention can be used to detect SDMA in biological samples from an animal subject. In the various aspects of the invention, the presence or amount of SDMA is determined. The amount of SDMA in a sample can be used to determine renal function and diagnose renal disease in an animal.

In a further aspect, SDMA analogs can be used to diagnose systemic lupus erythematosus (SLE) in an animal subject.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention, and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
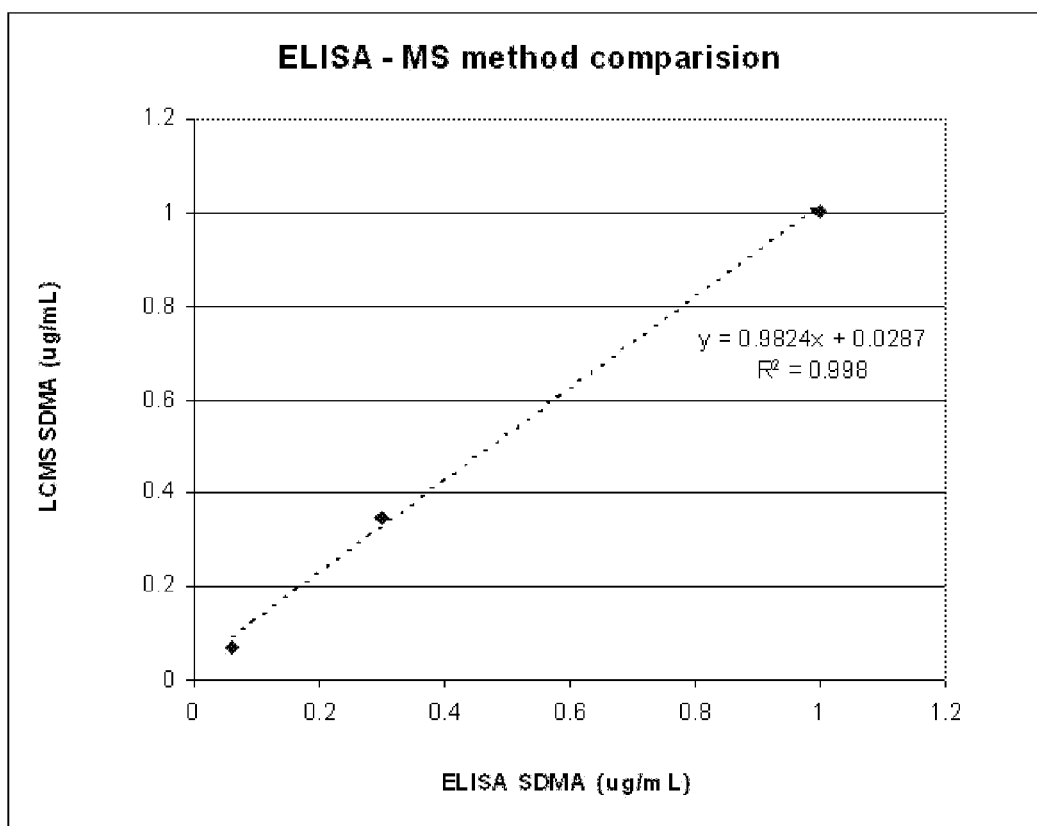
FIG. 1 is a graph comparing the results of the method of detecting SDMA according to the invention with mass spectroscopy.

In various aspects, the invention provides a method for detecting SDMA in a biological sample from an animal. The method includes detecting the presence or amount of SDMA in the sample by using an immunoassay format, such as a competitive immunoassay. The assay includes the use of antibodies to SDMA that are specific for SDMA and that have little or no cross-reactivity with ADMA, L-arginine and N-methylarginine. The assay also uses SDMA analogs that are connected to labels and/or solid phases. The presence or amount of SDMA in a sample can be used to diagnose or predict the disease state of the animal, such as renal disease, cardiovascular disease and SLE.

Before describing the invention in further detail, a number of terms are defined:

Ab is antibody.
ADMA is asymmetrical dimethylarginine. The structure of ADMA is:

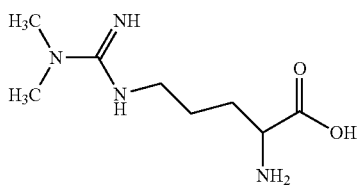

BUN is blood urea nitrogen.
BSA is bovine serum albumin.
CMIA is chemiluminescent magnetic immunoassay.
DCM is dichloromethane.
DIPEA is N,N-diisopropylethylamine.
DMF is dimethyl formamide.
EIA is enzyme immunoassay.
ELISA is enzyme-linked immunosorbent assay.
ESI-MS is electrospray ionization mass spectroscopy.
FPIA is fluorescence polarization immunoassay.
GFR is glomerular filtration rate.
HATU is (1H-7-azabenzotriazol-1-yl)-1,1,3,3-tetramethyl uranium hexafluorophosphate methanamininium.
KLH is keyhole limpet hemocyanin.
MEIA is microparticle enzyme immunoassay.
NOS is nitric oxide synthase.
PBS is phosphate buffered saline.
RIA is radioimmunoassay.

SDMA is symmetrical dimethylarginine. The structure of SDMA is:

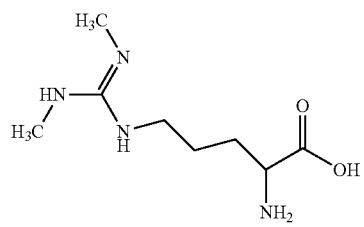

Free SDMA refers to SDMA that is not part of a polypeptide chain.
One or more amino acid residues of SDMA can be present in a polypeptide.
SLE is systemic lupus erythematosus.
TFA is trifluoroacetic acid.
The structure of arginine is:

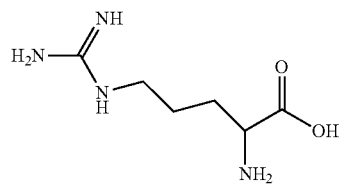 [SMILES: N=C(N)NCCCC(N)C(=O)O]

N-MMA is N-monomethylarginine, or simply N-methylarginine. The structure of N-monomethylarginine is:

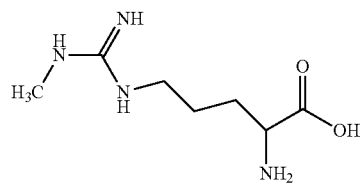

The term "analog," as used herein, generally refers to a compound in which one or more individual atoms have been replaced with a different atom(s) or with a different functional group(s). For example, an analog may be a modified form of the analyte which can compete with the analyte for a receptor, the modification providing a means to join the analyte to another moiety, such as a label or solid support. The analyte analog can bind to an antibody in a manner similar to the analyte.

The term "antibody," as used herein, generally refers to a glycoprotein produced by B lymphocyte cells in response to exposure to an antigen and binds specifically to that antigen. The term "antibody" is used in its broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, an "anti-SDMA," "anti-SDMA antibody portion," or "anti-SDMA antibody fragment" and/or "anti-SDMA antibody variant" and the like include any protein or peptide containing molecule that comprises at least a portion of an immunoglobulin molecule, such as, but not limited to, one complementarity determining region (CDR) of a heavy chain or light chain constant region, a framework region, or any portion thereof.

The term "antibody fragment," as used herein, refers to a portion of a full length antibody, generally the antigen binding or variable domain thereof. Specifically, for example, antibody fragments may include Fab, Fab', F(ab')$_2$, and Fv fragments; diabodies; linear antibodies; single-chain antibody molecules; and multispecific antibodies from antibody fragments.

The term "antigen," as used herein, generally refers to a substance that is capable, under appropriate conditions, of reacting with an antibody specific for the antigen.

The term "analyte," as used herein, generally refers to the substance, or set of substances in a sample that are detected and/or measured.

The term "biological sample," as used herein, generally refers to a sample of tissue or fluid from a human or animal including, but not limited to whole blood, plasma, serum, spinal fluid, lymph fluid, abdominal fluid (ascites), the external sections of skin, respiratory, intestinal and genitourinary tracts, tears, saliva, urine, blood cells, tumors, organs, tissue, and sample of in vitro cell culture constituents.

The term "cross-reactivity," as used herein, generally refers to the ability of an individual antigen binding site of an antibody to react with more than one antigenic determinant or the ability of a population of antibody molecules to react with more than one antigen. In general, cross reactions arise because (i) the cross reacting antigen shares an epitope in common with the immunizing antigen or (ii) it has an epitope which is structurally similar to one on the immunizing antigen (multispecificity).

The term "immunoassay," as used herein, generally refers to a test that employs antibody and antigen complexes to generate a measurable response. An "antibody:antigen complex" may be used interchangeably with the term "immunocomplex." Immunoassays, in general, include noncompetitive immunoassays, competitive immunoassays, homogeneous immunoassays, and heterogeneous immunoassays. In "competitive immunoassays," unlabeled analyte (or antigen) in the test sample is measured by its ability to compete with labeled antigen in the immunoassay. The unlabeled antigen blocks the ability of the labeled antigen to bind because the binding site on the antibody is already occupied. In "competitive immunoassays," the amount of antigen present in the test sample is inversely related to the amount of signal generated from the label. Conversely, in "noncompetitive immunoassays," also known as "sandwich" immunoassays, the analyte is bound between two highly specific antibody reagents to form a complex and the amount of antigen is directly proportional to the amount of signal associated with the complex. Immunoassays that require separation of bound antibody:antigen complexes are generally referred to as "heterogeneous immunoassays," and immunoassays that do not require separation of antibody:antigen complexes are generally referred to as "homogeneous immunoassays." One of skill in the art would readily understand the various immunoassay formats.

The term "immune complexes," as used herein, generally refers to the complexes formed by the binding of antigen and antibody molecules, with or without complement fixation. When one of either the antibody or antigen is labeled, the label is associated with the immune complex as a result of the binding between the antigen and antibody. Therefore, when the antibody is labeled, the label becomes associated with the antigen as a result of the binding. Similarly, when the antigen is labeled (e.g., an analyte analog having a label), the label becomes associated with the antibody as a result of the binding between the antigen and the antibody.

The term "label," as used herein, refers to a detectable compound, composition, or solid support, which can be conjugated directly or indirectly (e.g., via covalent or non-covalent means, alone or encapsulated) to an antibody, SDMA analog, or antigen of the invention. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current invention could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptacidin, digioxigenin, maltose, oligohistidine, 2,4-dinitrobenzene, phenylarsenate, ssDNA, dsDNA, and the like). The label may be bound to another molecule or solid support and that is chosen for specific characteristics that allow detection of the labeled molecule. The utilization of a label produces a signal that may be detected by means such as detection of electromagnetic radiation or direct visualization, and that can optionally be measured.

The term "monoclonal antibody," as used herein generally refers to an antibody obtained from a population of substantially homogeneous antibodies, i.e., the individual antibodies comprising the population are identical. Monoclonal antibodies are highly specific, being directed against a single antigenic site. In contrast to polyclonal antibody preparations, which typically include different antibodies directed against different epitopes, each monoclonal antibody is directed against a single epitope on the antigen. The modifier "monoclonal" merely refers to the character of the antibody and is not to be construed as requiring production of the antibody by any particular method. Specifically, for example, monoclonal antibodies may be made by hybridoma methodologies, or may be made by recombinant DNA methods, or may be isolated from phage antibody libraries using known techniques.

The term "polypeptide," as used herein, generally refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and polypeptide derivatives.

The term "solid support," as used herein, refers to a non-aqueous matrix to which the antibody or SDMA analog of the present invention can adhere. Example of solid support include supports formed partially or entirely of glass (e.g., controlled pore glass), synthetic and natural polymers, polysaccharides (e.g., agarose), polyacrylamides, polystyrene, polyvinyl alcohols and silicones, magnetic particles, latex particles, chromatographic strips, microtiter polystyrene plates, or any other substances that will allow bound antigens and/or antibodies to be washed or separated from unbound materials. In certain embodiments, depending on the application, the solid support can be the well of an assay plate or can be a purification column (e.g., an affinity chromatography column).

"Receptor" refers to any compound or composition capable of recognizing a particular spatial and polar organization of a molecule, e.g., epitopic or determinant site. Illustrative receptors include antibodies, Fab fragments, and the like.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide. For example, "specificity," as used herein, generally refers to the ability of an individual antibody combining site to react with only one antigenic determinant or the ability of a population of antibody molecules to react with only one antigen. In general, there is a high degree of specificity in antigen-antibody reactions. Antibodies can distinguish differences in (i) the primary structure of an antigen, (ii) isomeric forms of an antigen, and (iii) secondary and tertiary structure of an antigen. Antibody-antigen reactions that exhibit high specificity exhibit low cross reactivity.

"Substantial binding" or "substantially bind" refers to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, less than 10%, less than 5% or less than 1% of the reactivity exhibited toward a third molecule under a particular set of assay conditions. Specific binding can be tested using a number of widely known methods, e.g., an immunohistochemical assay, an enzyme-linked immunosorbent assay (ELISA), a radioimmunoassay (RIA), or a western blot assay.

The term "salt," as used herein, means a salt formed between an acid and a basic functional group of a compound. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "salt" also refers to a salt formed between a compound having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

Turning now to the various aspects of the invention, one aspect the invention is directed to an immunological method, devices and kits for detecting the presence of an amount of free SDMA in a biological sample. The method may include controls, calibrators or standards comprising one or more SDMA analogs. In particular, the method may be accomplished using immunoassay techniques well known to those of skill in the art, including, but not limited to, using microplates and lateral flow devices. Animal subjects from which samples are obtained for detecting SDMA, include human and non-human animals (e.g., companion animals, livestock, etc.) subjects. The determination of disease states associated with the presence or amount of SDMA can be conducted for both human and non-human subjects.

The solid phase assay format is a commonly used binding assay technique. There are a number of assay devices and procedures wherein the presence of an analyte is indicated by the analyte's binding to a conjugate and/or an immobilized complementary binding member. In one particular aspect, the immobilized binding member (e.g., anti-SDMA antibody) is bound, or becomes bound during the assay, to a solid phase such as a reaction well, dipstick, test strip, flow-through pad, paper, fiber matrix or other suitable solid phase material. The binding reaction between free SDMA in the sample and immobilized antibody is determined by adding to the sample an amount of an analog of SDMA, which includes SDMA conjugated to a label. After contacting the mixture of the sample and the SDMA analog to the solid phase, the mixture and solid phase are incubated to allow for binding between the immobilized antibody, the SDMA and the SDMA analog. Following the incubation, unbound reactants are removed from the solid phase. The amount of the label that becomes associated with the antibody through binding of the antibody to the analog is measured. The amount of the label associated with the antibody is inversely proportional to the amount of free SDMA in the sample.

Immobilization of one or more antibodies to SDMA onto a device or solid support is performed so that the antibodies will not be washed away by the sample, diluent and/or wash procedures. One or more antibodies can be attached to a surface by physical adsorption (i.e., without the use of chemical linkers) or by chemical binding (i.e., with the use of chemical linkers). Chemical binding can generate stronger attachment of antibodies on a surface and provide defined orientation and conformation of the surface-bound molecules.

In another aspect, SDMA antibodies raised in a particular species are bound to a solid support by interaction with an anti-species antibody that is bound to the support. In one particular aspect, anti-SDMA antibodies are raised in rabbits, and the support has bound thereto anti-rabbit antibody that recognizes the anti-SDMA antibody raised in rabbits. In this aspect, the antibody may be in the form of anti-serum obtained from the species. The anti-SDMA antibodies can either be applied to the solid phase having the anti-species antibody prior to adding the sample to the solid phase, or the anti-SDMA antibodies can be mixed with the sample prior to adding the sample to the solid phase. In either case, the anti-SDMA antibodies become bound to the solid phase through binding to the anti-species antibody on the solid phase.

In another aspect, the invention includes one or more labeled antibodies that can be mixed with a test sample prior to application of the mixture to a solid support. In this case, an SDMA analog can be attached to the solid support so that the analog will not be washed away by the sample, diluent and/or wash procedures. Labeled antibodies in the sample bind to SDMA in the sample and are, therefore, not available for binding with the SDMA analog on the solid support. After application of the mixture to the solid support, and an appropriate incubation, the mixture is washed from the solid support. Antibodies that have not bound to sample SDMA will become bound to the SDMA analog on the solid support. The presence or amount of SDMA in the sample is inversely proportional to the amount of antibody that has become bound to the SDMA analog. The signal associated with the label on the antibody can be measured by the appropriate method.

FIG. 1 shows a comparison of the method of detecting SDMA in pooled canine sera spiked with SDMA according to the invention and the detection of SDMA using mass spectroscopy. As shown, the SDMA concentrations values obtained from the method of the invention strongly correlate with those obtained using MS.

The detection of free SDMA in a biological sample from an animal can provide an indication of renal function in the animal. Renal diseases and disorders (e.g., kidney impairment, renal insufficiency, chronic kidney disease, glomerulonephritis, diabetic nephropathy, interstitial nephritis, polycystic kidney disease, and hypertensive kidney disease) tend to decrease overall renal function, including GFR, and can be diagnosed in a number of ways, including use of common renal markers creatinine and BUN. By comparing the level of SDMA, BUN and creatinine in healthy and diseased animals, the level of SDMA in a sample can be related to the disease state of the animal. Accordingly, "healthy" animals showing normal (reference range) creatinine and BUN will have lower SDMA levels than those of diseased animals. In general, animals suffering from a renal disorder/disease will have higher serum SDMA levels than animals with normal renal function. In healthy humans, plasma SDMA levels typically range from 0.3-0.7 µmol/l (J Am Soc Nephrol (2006) 17: 1128-1134; Eur J Clin Invest. 2007 June; 37(5): 364-371. Nephrol Dial Transplant (2003) 18: 2542-2550; Nephrol Dial Transplant (2006) 21: 2446-2451; Kidney International, (2001) 59 (78): S14-S18).

Figure 2:
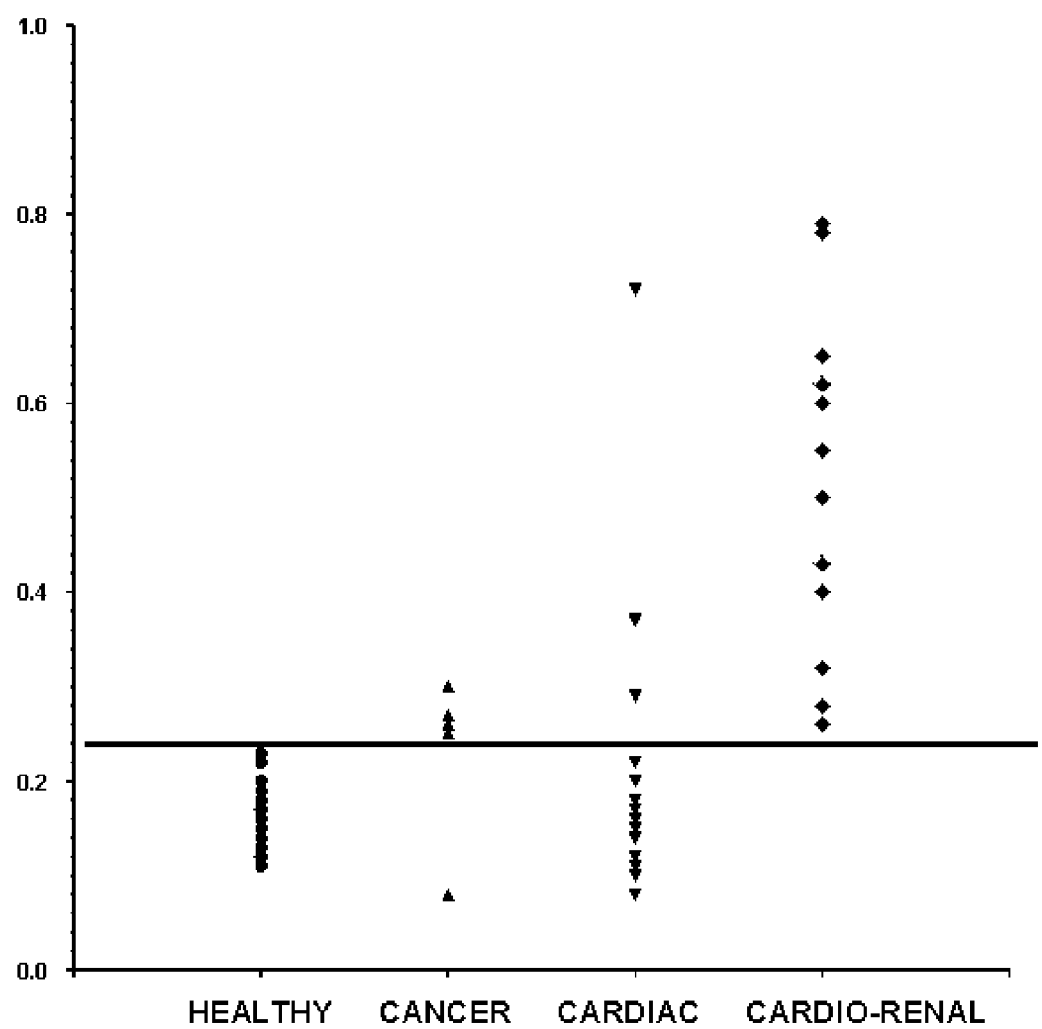
FIG. 2 is a plot of SDMA concentrations measured according to the method of the invention in healthy dogs and dogs having cancer, cardiac disease, or cardio-renal disease. The horizontal bar represents the cutoff value (determined as mean SDMA concentration plus 2 standard deviations from a population of healthy dogs).
Figure 3:
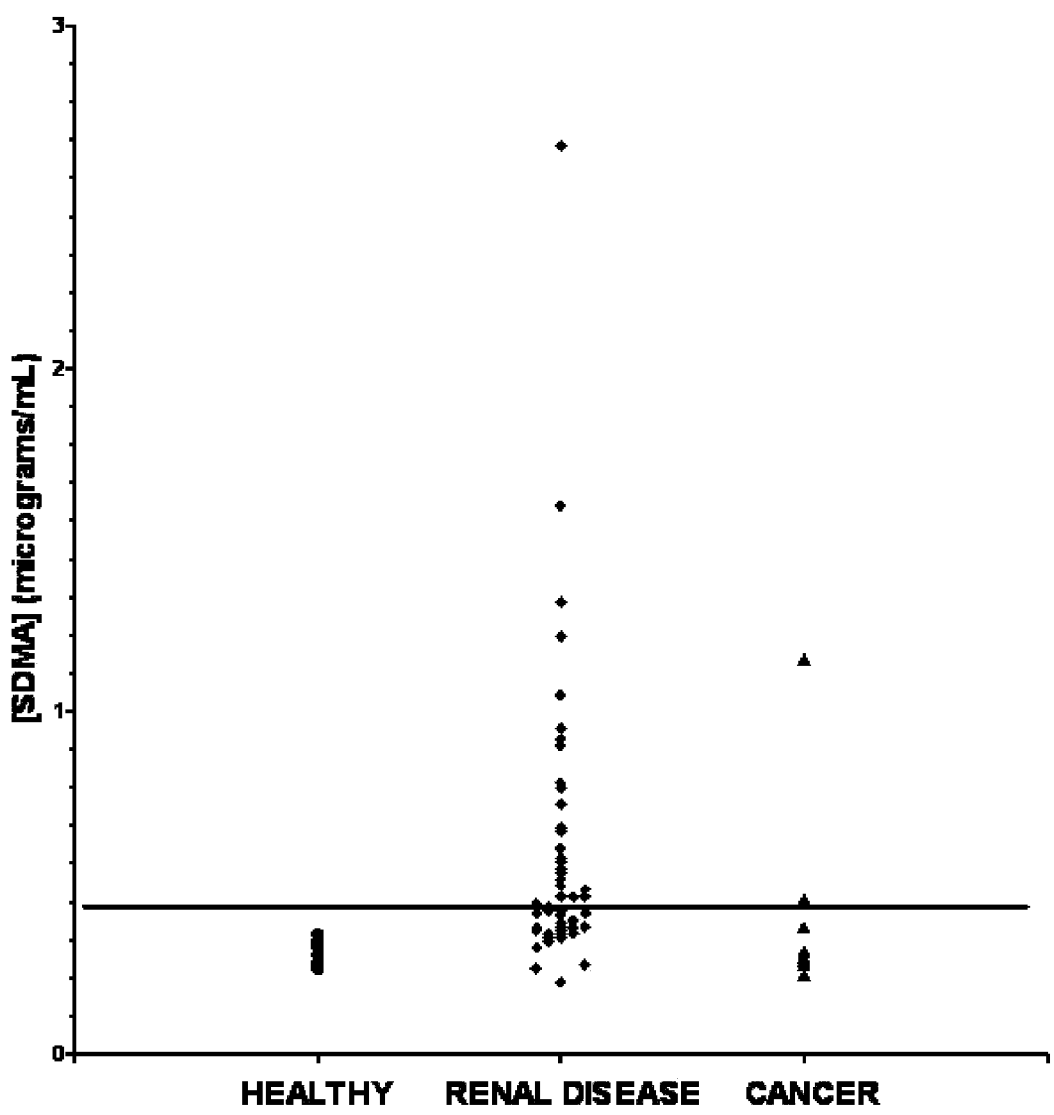
FIG. 3 is a plot of SDMA concentrations measured according to the method of the invention in healthy cats and cats having renal disease or cancer. The horizontal bar represents the cutoff value (determined as mean SDMA concentration plus 2 standard deviations from a population of healthy cats).
Figure 4:
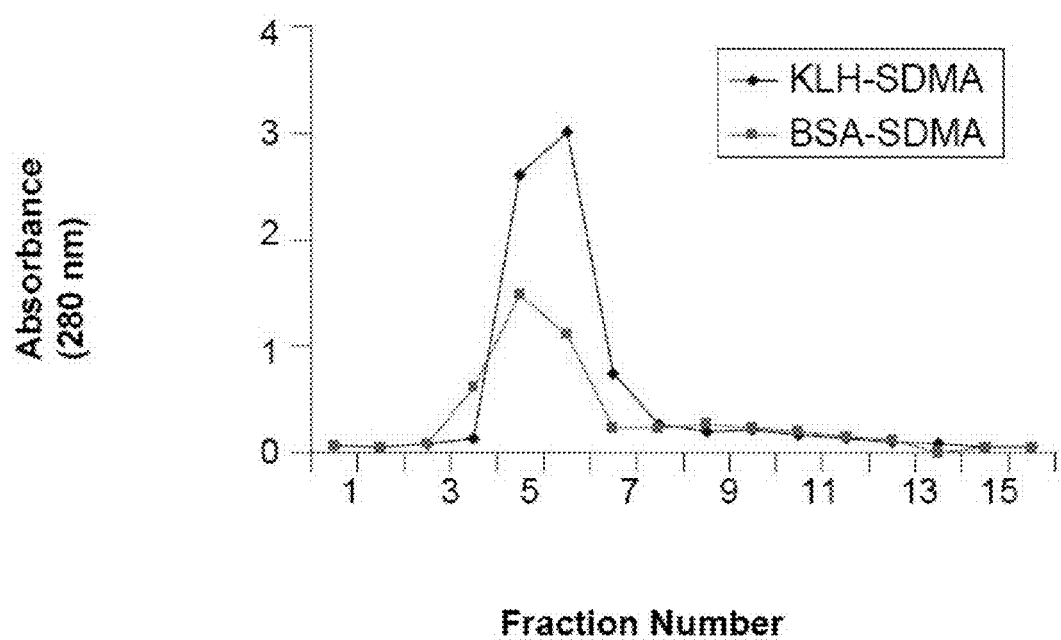
FIG. 4 is a plot of absorbance at 280 nm v. fraction number for elution of an SDMA cystamide protein conjugate, wherein the protein is KLH (♦) or BSA (■), from a Sephadex G-25M gel-filtration column as described in the Examples.

Similarly, the level of free SDMA in a biological sample can be used as a marker of cardiac disease in the animal. The level of SDMA in the sample can be compared to levels of known markers for cardiac disease to determine a cut-off range for diagnosing cardiac disease (J Am Soc Nephrol (2006) 17: 1128-1134). As shown in FIGS. 2 and 3, the method of the invention was used to determine SDMA concentrations in healthy dogs (FIG. 2) and cats (FIG. 3), and in cats and dogs suffering from cancer, cardiac and renal diseases. Animals suffering from renal disease had higher levels of SDMA than healthy animals.

Detection of the antibody:antigen complexes may be achieved through a variety of techniques well know in the art, such as, for example, turbidimetry, enzymatic labeling, radiolabeling, luminescence, or fluorescence. Immunoassay methodologies are known by those of ordinary skill in the art and are appreciated to include, but not limited to, radioimmunoassay (RIA), enzyme immunoassays (EIA), fluorescence polarization immunoassays (FPIA), microparticle enzyme immunoassays (MEIA), and chemiluminescent magnetic immunoassays (CMIA). In RIA, an antibody or antigen is labeled with radioactivity and used in a competitive or noncompetitive format. In EIA, an antibody or antigen is labeled with an enzyme that converts a substrate to a product with a resulting signal that is measured, such as a change in color. In FPIA, an antigen is labeled with fluorescent label and competes with unlabeled antigen from the specimen. The amount of analyte measured is inversely proportional to the amount of signal measured. In MEIA, a solid phase microparticle is coated with antibodies against an antigen of interest and is used to capture the analyte. The antibody for detection is labeled with an enzyme as in the EIA method. The concentration of analyte measured is proportional to the amount of signal measured. In CMIA, a chemiluminescent label is conjugated to the antibody or antigen, and produces light when combined with its substrate. CMIA can be configured in a competitive or non-competitive format, and yields results that are inversely or directly proportional to the amount of analyte present, respectively.

The use of reagent-impregnated test strips in specific binding assays is also well-known. In such procedures, a test sample is applied to one portion of the test strip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the test strip, wherein a complementary binding member to the analyte is immobilized. The extent to which the analyte becomes bound in the detection zone can be determined with the aid of the conjugate which can also be incorporated in the test strip or which can be applied separately. In one embodiment, an antibody specific for SDMA is immobilized on a solid support at a distinct location. Following addition of the sample, detection of SDMA-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present invention.

Other detection technologies employ magnetic particles or microbeads, for example, superparamagnetic iron oxide impregnated polymer beads. These beads are associated with, for example, a specific binding partner for the analyte. The beads bind with the target analytes in the sample being tested and are then typically isolated or separated out of solution magnetically. Once isolation has occurred, other testing may be conducted, including observing particular images or labels, whether directly optically or by means of a camera.

In a further aspect, the invention relates to SDMA analogs and methods for their production and use, particularly thiol-containing, hydroxyl-containing, amino containing, and carboxylate containing SDMA analogs, where the thiol group, hydroxyl group, amino group, or carboxylate group enables the SDMA to be linked to another molecule (conjugation target), such as an activated protein, to form an SDMA conjugate. The SDMA analogs of the invention enable SDMA to be linked to a conjugation target such as a protein, polypeptide, detectable label, solid support, and the like to provide the SDMA conjugate. The SDMA conjugates of the invention can be used to produce antibodies for use in immunoassays specific for SDMA. The antibodies of the invention have little or no cross-reactivity with arginine, ADMA, and/or monomethylarginine. The SDMA analogs of the invention can also be conjugated to a label for use in immunoassays specific for SDMA.

The SDMA analogs of the invention may have the following structures:

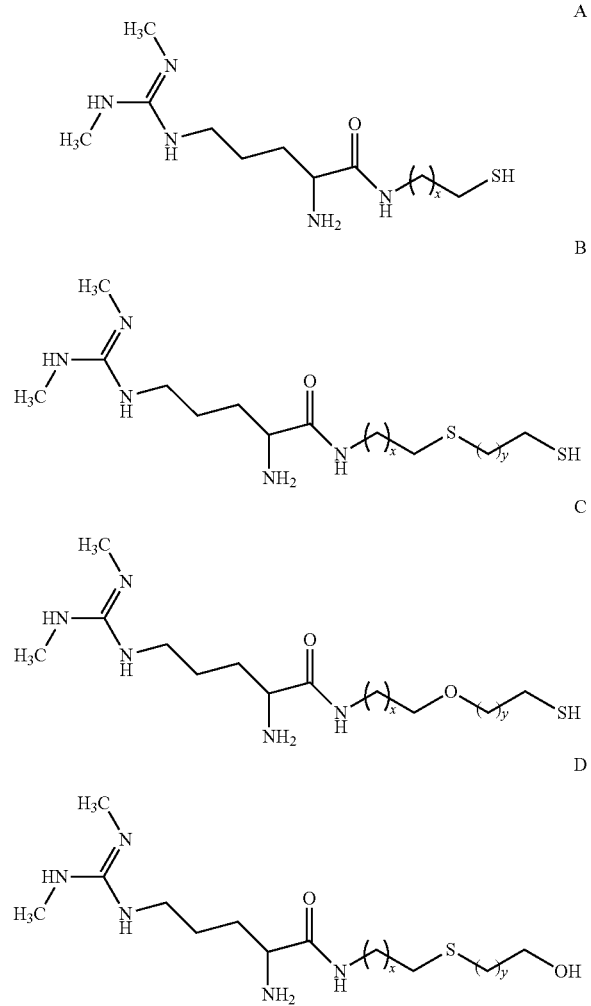

wherein x and y are integers ranging from 1 to 5.

According to one embodiment, the SDMA analogs of the invention have the following general formula:

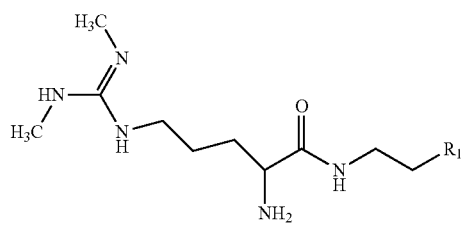

where $R_1$ may be a thiol (or protected thiol), a hydroxyl (or protected hydroxyl), an amino (or protected amino) group, or a carboxylate (including carboxylic acid) or protected carboxylate group.

Suitable thiol, hydroxyl, amino, and carboxylate protecting groups are known to those skilled in the art such as those described, for example, in T. W. Greene, et al. *Protective Groups in Organic Synthesis,* 3rd ed. (1999).

In one particular embodiment, the invention is directed to an SDMA analog of formula (3):

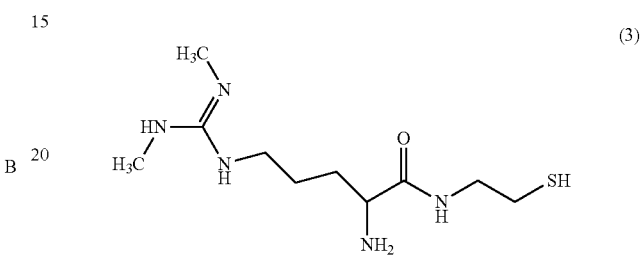

or a salt thereof. The compound of formula (3) provides an available thiol that can react with a conjugation target that includes an appropriate "thiol-reactive site," i.e., a site that will react with a thiol group. For example, maleimides, alkyl and aryl halides, and alpha-haloacyls are illustrative thiol-reactive sites that can react with thiols to form thio-ethers. Similarly, pyridyl disulfides can react with thiols to form mixed disulfides.

In another embodiment, $R_1$ is X—$R_2$, wherein X is —S—, —O—, —N—, or, —COO— and $R_2$ is a label having a thiol, hydroxyl, amino, or carboxylate reactive group.

In one embodiment, $R_1$ is X—$R_2$, wherein X is —S—, —O—, —N—, or, —COO— and $R_2$ is a protein that has been functionalized to include a thiol, hydroxyl, amino, or carboxylate reactive group.

In one embodiment, SDMA is conjugated to a carrier protein to form a "hapten-carrier" immunogen that can be used to stimulate an immune response to an epitope that includes SDMA. Exemplary immunogenic proteins include, but are not limited to, BSA, KLH, and ovalbumin. Protocols for conjugating haptens to immunogenic proteins are known in the art (see, e.g., Antibodies: A Laboratory Manual, E. Harlow and D. Lane, eds., Cold Spring Harbor Laboratory (Cold Spring Harbor, N.Y., 1988) pp. 78-87).

In one embodiment, the SDMA analog is conjugated to a maleimide activated protein, such as, for example, maleimide activated keyhole limpet protein (KLH) or maleimide activated bovine serum albumin (BSA).

In one embodiment, the compound of formula (3) is conjugated to a maleimide activated protein, such as, for example, maleimide activated keyhole limpet protein (KLH) or maleimide activated bovine serum albumin (BSA).

Thus, in a specific embodiment, the invention relates to a conjugate of a compound of formula (3) and maleimide activated protein having the formula:

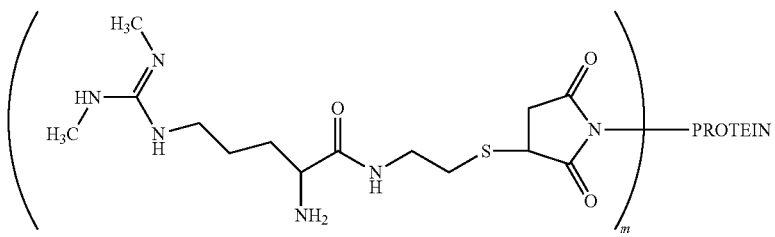

wherein m is an integer.

Typically, m is greater than 5. However, the value for m is variable. For example, m is about 15 maleimide groups per protein in maleimide activated BSA commercially available from Sigma-Aldrich of St. Louis, Mo.; m is about 80 maleimide groups per protein in maleimide activated KLH commercially available from Sigma-Aldrich; m is in a range of about 15 to about 25 maleimide groups per protein in maleimide activated BSA commercially available from Thermo Scientific Pierce Protein Research Products of Rockford, Ill.; m is greater than about 400 maleimide groups per protein in maleimide activated KLH commercially available from Thermo Scientific Pierce Protein Research Products; and m is in a range of about 150 to about 300 maleimide groups per protein in maleimide activated KLH commercially available from A. G. Scientific of San Diego, Calif. In general, m is limited by the number of available amine groups present in an immunogenic protein. The number of available amines can be increased by conjugating the immunogenic protein to polyamines.

In one embodiment, PROTEIN is BSA and m is greater than about 5. In one embodiment, PROTEIN is BSA and m is greater than about 10. In one embodiment, PROTEIN is BSA and m is greater than about 25. In one embodiment, PROTEIN is BSA and m is greater than about 50. In one embodiment, PROTEIN is BSA and m is greater than about 75. In one embodiment, PROTEIN is BSA and m is in a range of about 5 to about 80. In one embodiment, PROTEIN is BSA and m is greater than about 75. In one embodiment, PROTEIN is BSA and m is in a range of about 10 to about 80. In one embodiment, PROTEIN is BSA and m is greater than about 75. In one embodiment, PROTEIN is BSA and m is in a range of about 20 to about 80. In one embodiment, PROTEIN is BSA and m is greater than about 75. In one embodiment, PROTEIN is BSA and m is in a range of about 30 to about 80.

In one embodiment, PROTEIN is KLH and m is greater than about 5. In one embodiment, PROTEIN is KLH and m is greater than about 50. In one embodiment, PROTEIN is KLH and m is greater than about 100. In one embodiment, PROTEIN is KLH and m is greater than about 200. In one embodiment, PROTEIN is KLH and m is greater than about 300. In one embodiment, PROTEIN is KLH and m is greater than about 400. In one embodiment, PROTEIN is KLH and m is greater than about 500. In one embodiment, PROTEIN is KLH and m is greater than about 600. In one embodiment, PROTEIN is KLH and m is greater than about 700. In one embodiment, PROTEIN is KLH and m is greater than about 800. In one embodiment, PROTEIN is KLH and m is in a range of about 5 to about 800. In one embodiment, PROTEIN is KLH and m in a range of about 5 to about 600. In one embodiment, PROTEIN is KLH and m in a range of about 5 to about 400. In one embodiment, PROTEIN is KLH and m in a range of about 5 to about 200. In one embodiment, PROTEIN is KLH and m in a range of about 5 to about 100. In one embodiment, PROTEIN is KLH and m in a range of about 100 to about 200. In one embodiment, PROTEIN is KLH and m ranges in a range of 100 to about 300. In one embodiment, PROTEIN is KLH and m in a range of about 100 to about 400. In various aspects, PROTEIN is KLH and m in a range of about 100 to about 500, about 100 to about 600, about 100 to about 700, about 100 to about 800, or about 100 to about 1,000.

The conjugate of a compound of formula (3) and maleimide activated protein can be characterized using methods well known to those skilled in the art (see, for example, Sigma-Aldrich Technical Bulletin for Maleimide Activated BSA, KLH Conjugation Kit (catalog no. MBK1)).

In an alternate embodiment, the SDMA analog is linked to a detectable label through the thiol, hydroxyl, amino, or carboxylate group. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label may be a specific binding molecule which itself may be detectable (e.g., biotin, avidin, streptavidin, digioxigenin, maltose, oligohistidine, 2,4-dinitrobenzene, phenylarsenate, ssDNA, dsDNA, etc.). The SDMA can be linked to a detectable label using methods well known to those skilled in the art. As an illustrative example, the SDMA analog can be linked to maleimide activated peroxidase, from horseradish lyophilized powder, greater than about 200 units/mg protein (commercially available from Sigma-Aldrich St. Louis, Mo. (catalog no. P1709) following the directions in the product manual).

The analog of formula (3) may be prepared from SDMA (commercially available from EMD Chemicals Inc. of Gibbstown, N.J.) by the following illustrative synthetic scheme (1):

Scheme 1:

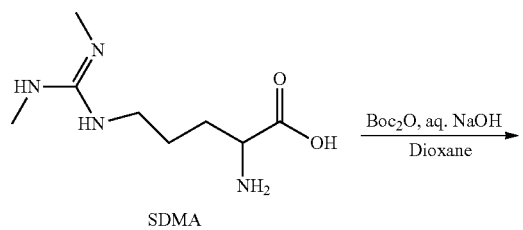

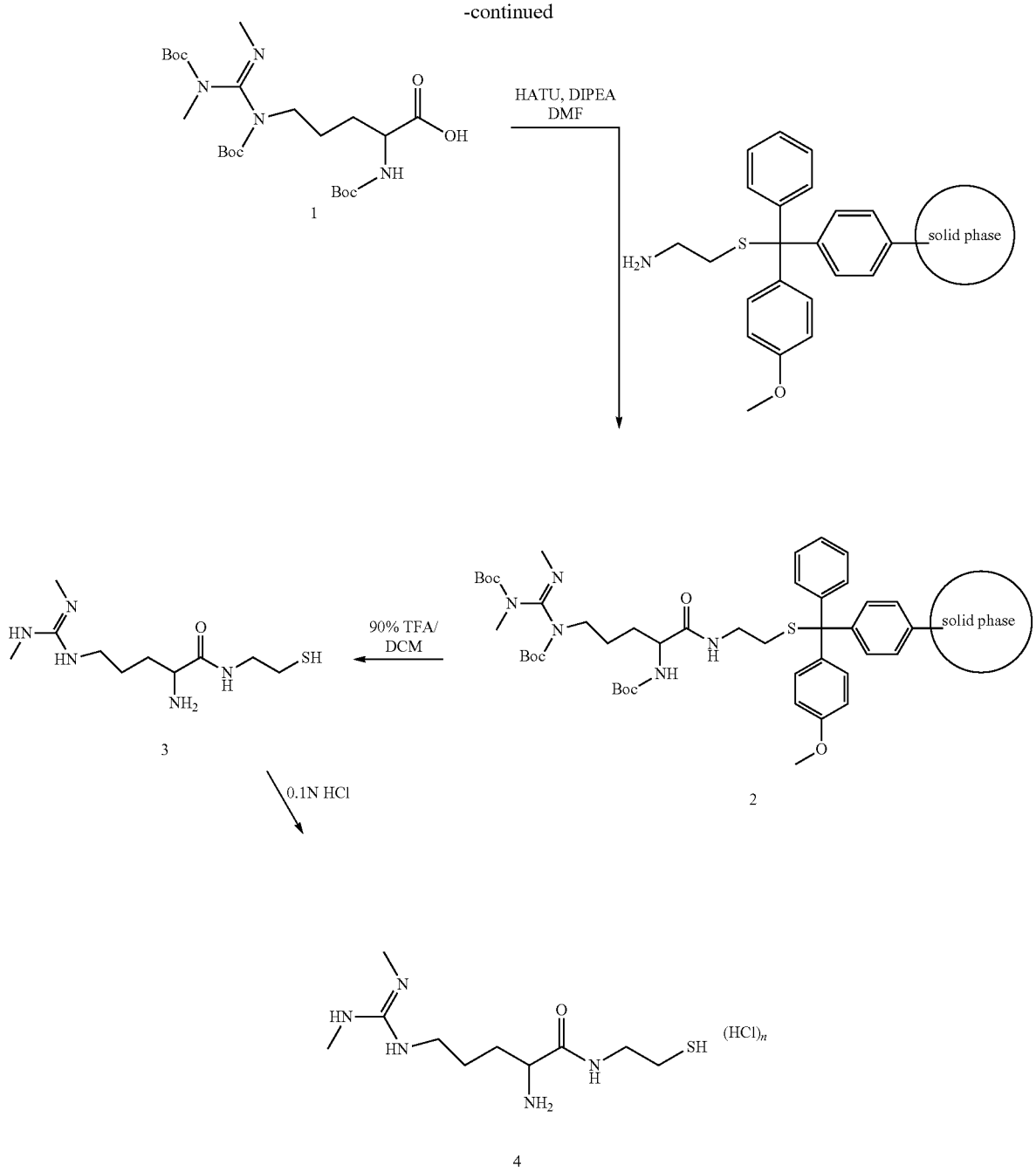

The primary and secondary amino groups of SDMA are protected by reacting SDMA with di-tert-butyldicarbonate (Boc$_2$O). The resulting tert-butoxycarbonyl (BOC) protected SDMA ((Boc$_3$)-SDMA, 1) is then linked to a resin. For example, the (Boc$_3$)-SDMA (1) can be linked to a cysteamine-4-methoxy trityl resin (commercially available from EMD Chemicals, Inc. of Gibbstown, N.J.) by contacting the (Boc$_3$)-SDMA (1) with the resin in the presence of 2-(1H-7-azabenzotriazol-1-yl)-1,1,3,3-tetramethyl uranium hexafluorophosphate methanamininium (HATU) and N,N-diisopropylethylamine (DIPEA) in dimethyl formamide (DMF) to provide resin bound (Boc$_3$)-SDMA cystamide (2).

The BOC protecting groups on the resin bound (Boc$_3$)-SDMA cystamide (2) are removed and the resulting resin bound SDMA cystamide cleaved from the resin using, for example, trifluoroacetic acid in dichloromethane, to provide SDMA cystamide (3), which was converted to the hydrochloride salt (4) by reaction with hydrochloric acid.

The analogs of formula A-D, described above, can be made using similar methodologies as described in Scheme 1.

Maleimide activated protein can then be reacted with SDMA cystamide (3) to provide a SDMA cystamide protein conjugate as described below in Scheme II:

Scheme II:

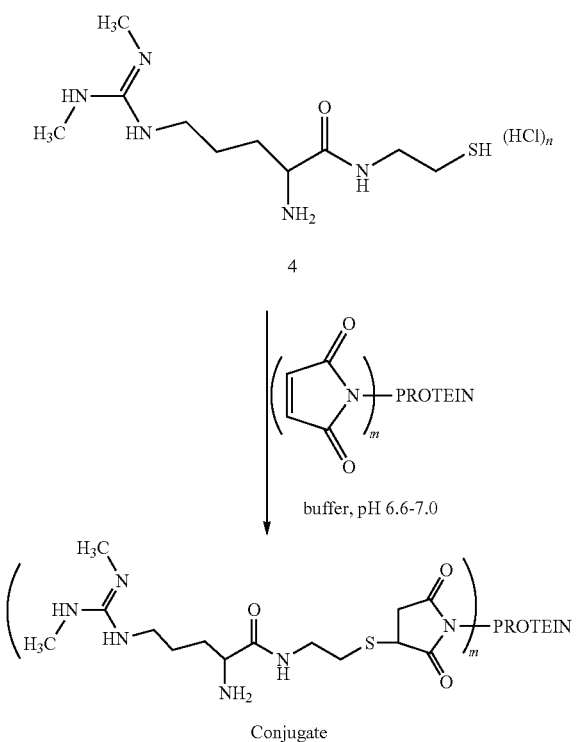

wherein n is an integer ranging from 1 to 3 and m is an integer as defined above.

The resulting conjugate can be purified using methods known to those skilled in the art including, but not limited to column chromatography, for example, using gel-filtration column chromatography with Sephadex (for example, Sephadex G-25M) as the solid support (commercially available from Sigma-Aldrich).

Conjugates of analogs A-D can be made using similar methodologies as described in Scheme 2.

The conjugate of the analog of formula A-D and maleimide activated KLH or maleimide activated BSA may be used as an immunogen to generate antibodies that substantially bind SDMA (i.e., anti-SDMA antibodies) and show no or substantially no cross reactivity with ADMA, L-arginine, and/or N-methylarginine, The conjugate of the analog of formula (3) and maleimide activated KLH or maleimide activated BSA may be used as an immunogen to generate antibodies that substantially bind SDMA (i.e., anti-SDMA antibodies). Such antibodies show no or substantially no cross reactivity with ADMA, L-arginine, and/or N-methylarginine.

The invention also relates to isolated, recombinant, synthetic, and/or in vivo-produced anti-SDMA antibodies. The invention further includes, but is not limited to, methods of making and using such antibodies, including diagnostic and therapeutic compositions, methods, and devices. Anti-SDMA antibodies useful in the methods and compositions of the invention are characterized by a high affinity binding to SDMA with little or no cross-reactivity to ADMA, arginine, and/or monomethylarginine. The anti-SDMA antibodies of the invention are useful, for example, as a diagnostic marker for renal function, such as kidney impairment, renal insufficiency, glomerular filtration rate (GFR), inulin clearance, and creatinine clearance, and for renal disorders/diseases, such as chronic kidney disease, glomerulonephritis, diabetic nephropathy, interstitial nephritis, polycystic kidney disease, and hypertensive kidney disease; as well as other diseases/disorders, such as SLE, cardiac disease, and hepatic failure.

In one embodiment, the generated antibodies are able to detect free SDMA (i.e., SDMA not part of a polypeptide chain) and show no or substantially no cross-reactivity with ADMA, L-arginine, and/or N-methylarginine. As shown in the Examples, antibodies of the invention show less than 1% cross reactivity with ADMA, L-arginine and/or N-methylarginine, based on equal concentrations of the antigens. As generally understood in the art, the impact of cross-reactivity will depend on the relative abundance of the cross-reacting antigen (e.g., ADMA, L-arginine and/or N-methylarginine) as compared to the immunizing antigen (SDMA) in a test sample. For example, a cross-reactivity as high as 50% may be acceptable if the concentration of the immunizing antigen is 100-fold greater than that of the cross-reacting antigen. Conversely, a cross-reactivity as low as 1% may be problematic if the concentration of the cross-reacting antigen is 100-times that of the immunizing antigen. Accordingly, the impact of cross-reactivity must be considered in context of the relative abundances of any cross-reacting antigens and the immunizing antigen, in the sample to be analyzed. In the various aspects of the invention, cross reactivity does not affect the substantial binding of SDMA or SDMA analog to an anti-SDMA antibody.

The methods for making the antibodies of the invention may include using one or more SDMA conjugates as an immunogen to stimulate an immune response. The methods include administering one or more SDMA conjugates to an animal using a suitable immunization protocol, and separating an appropriate antibody from a body fluid(s) of the animal, as described, for example, in Example 3, infra. Alternatively, the SDMA conjugates of the invention may be used in phage display methods to select phage displaying on their surface an appropriate antibody, followed by separation of nucleic acid sequences encoding at least a variable domain region of an appropriate antibody. Phage display methods are well known to those of ordinary skill in the art. (See, for example, Antibody Phage Display; Methods in Molecular Biology, Vol. 178, O'Brien, Philippa M.; Aitken, Robert (Eds.) 2002). Monoclonal antibodies to SDMA can be prepared by methods generally known in the art.

The SDMA analogs of the invention may be linked to a label to provide a detectable conjugate for use in receptor binding assays, such as immunoassays for SDMA. Similarly, the anti-SDMA antibodies can be linked to a label to provide detectable anti-SDMA antibodies for use in receptor binding assays, such as immunoassays for SDMA. The SDMA analogs and anti-SDMA-antibodies can be linked to a label using methods well known to those skilled in the art. E.g., Immunochemical Protocols; Methods in Molecular Biology, Vol. 295, edited by R. Burns (2005)). The detectable SDMA conjugate or detectable anti-SDMA antibodies may be used in various homogenous, sandwich, competitive, or non-competitive assay formats, to generate a signal that is related to the presence or amount of an SDMA in a test sample.

In a specific embodiment, the immunoassay methodologies are competitive immunoassays for detection of anti-SDMA antibodies. The competitive immunoassay may be carried out in the following illustrative manner. A sample, from an animal's body fluid, potentially containing anti-SDMA antibodies, is contacted with an SDMA analog conjugated to a solid support and with an anti-SDMA antibody conjugated to a detectable label of the invention.

The anti-SDMA antibodies of interest, present in the sample, compete with the anti-SDMA antibody conjugated to a detectable label for binding with the SDMA analog conjugated to a solid support. The amount of the label associated with the solid support can be determined after separating unbound antibodies and the solid support. In an alternative embodiment, the competitive immunoassay is carried out in the following illustrative manner. A sample, from an animal's body fluid, potentially containing anti-SDMA antibodies, is contacted with an SDMA analog linked to a detectable label and then with an antibody conjugated to a solid support. The anti-SDMA antibodies in the sample compete with the anti-SDMA antibodies on the solid support for binding with the SDMA conjugate linked to a detectable label. In either case, the signal obtained is inversely related to the amount of SDMA antibody of interest present in the sample.

In a specific embodiment, the anti-SDMA antibodies of the invention may be used to develop a competitive immunoassay to aid in the diagnosis of SLE in a patient. In general, patients suffering from SLE spontaneously produce autoantibodies against the SLE-specific proteins, i.e., the Sm proteins B/B', D1, D2, D3, E, F, and G. D1 and D3 are the most common antigens recognized by anti-Sm autoantibodies, which are an autoantibody population found exclusively in patients afflicted with SLE. Protein sequencing and mass spectroscopy have demonstrated that all arginines in the C-terminal arginine-glycine (RG) dipeptide repeats of the human Sm proteins D1 and D3 contain SDMA. Accordingly, the anti-SDMA antibodies of the invention may react with the SDMA present in the RG dipeptide repeats of D1 and D3.

In particular, the immunoassay for diagnosing SLE may be carried out in the following manner. In a reaction chamber, D1 and D3 proteins are immobilized on a solid support using methods well known to those of ordinary skill in the art. An aliquot of patient serum or plasma is added to the reaction chamber. If the patient sample contains anti-D1 and/or anti-D3 autoantibodies, the anti-D1 and/or anti-D3 autoantibodies will bind to the SDMA sites on the D1 and/or D3 proteins. Anti-SDMA antibodies of the invention conjugated to a label are then added to the reaction chamber. The labeled anti-SDMA antibodies will only bind to the SDMA site on the D1 and/or D3 proteins if the anti-D1 and/or anti-D3 autoantibodies do not saturate all of the SDMA sites present on the D1 and/or D3 protein. Accordingly, if the labeled anti-SDMA antibodies of the invention bind to the SDMA sites on the D1 and/or D3 protein, the results are indicative of the absence of anti-D1 and/or anti-D3 autoantibodies and may indicate that the patient is not afflicted with SLE. Conversely, however, if the labeled anti-SDMA antibodies of the invention do not bind to the SDMA sites on the D1 and/or D3 protein, this is indicative of the presence of anti-D1 and/or D3 autoantibodies, and that the patient is afflicted with SLE. As typical with competitive assays, the signal generated from the conjugated label in this assay will be inversely proportional to the amount of anti-D1 and/or anti-D3 autoantibodies present in the sample.

The invention further provides diagnostic kits containing reagents for use in detecting SDMA or anti-SDMA antibodies. Typically, such a kit contains at least one SDMA analog and/or at least one reagent that substantially binds to SDMA, such as an anti-SDMA antibody of the invention. Kits typically also includes directions or instructions describing how to perform the above-described diagnostic assays, and/or how to interpret the results thereby obtained. In some kits, anti-SDMA antibodies are linked to an immobilized solid support and/or the SDMA conjugate is an SDMA analog immobilized on a solid support. The anti-SDMA antibody or SDMA conjugate may or may not be linked to an appropriate label.

In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

Without further elaboration, it is believed that one skilled in the art using the preceding description can utilize the invention to the fullest extent. Other features and advantages of the invention will be apparent from the following Examples. The following are provided for exemplification purposes only and are not intended to limit the scope of the invention described in broad terms above. All references cited in this disclosure are incorporated herein by reference.

EXAMPLES

Example 1: Synthesis of the SDMA Cystamide (3) and SDMA Cystamide Hydrochloride Salt (4)

SDMA cystamide (3) was prepared according to the route of synthesis described in Scheme 1.

(BOC)$_3$-SDMA (1): To a solution of 4.36 g (20 mmol) di-tert-butyldicarbonate (Boc$_2$O) in 20 mL dioxane was added dropwise 550 mg (2.0 mmol) of N,N-dimethylarginine dihydrochloride (SDMA) (commercially available from EMD Chemicals Inc. of Gibbstown, N.J.) dissolved in 10 mL of 5.0 N NaOH over 30 minutes at room temperature with stirring. The resulting reaction mixture was stirred overnight. 30 mL of dichloromethane (DCM) and 30 mL of water were then added to the reaction mixture and the pH adjusted to 6.5 with acetic acid (AcOH). The DCM layer was separated, washed with brine, and dried over anhydrous $Na_2SO_4$. The DCM was then removed under reduced pressure to provide a solid. The resulting solid was washed 2 times with 10 mL of hexane. The solid was then dried under vacuum to provide 800 mg of a light yellow solid. Subsequent reactions did not require further purification. The solid was characterized by mass spectroscopy. ESI-MS: 525.7 $(M+Na)^+$, 503.6 $(M+1)^+$, 403.5 $(M-Boc+1)^+$, 303.5 $(M-2Boc+1)^+$.

$(Boc)_3$-SDMA-cystamine-resin (2): To a mixture of 600 mg (1.2 mmol) $(Boc)_3$-SDMA (1) and 627 mg (1.6 mmol) 2-(1H-7-Azabenzotriazol-1-yl)-1,1,3,3-tetramethyl uronium hexafluorophosphate methanaminium (HATU) in 15 mL of dimethylformamide (DMF) was added 420 μL (2.4 mmol) of N,N-diisopropylethylamine (DIPEA). The resulting mixture was then stirred for 20 minutes under a dry N2 atmosphere. Separately, cystamine 4-methoxy trityl resin (1.0 g) (commercially available from EMD Chemicals, Inc. of Gibbstown, N.J.) was swelled and washed using DMF. The swelled resin was then added to the reaction mixture and the reaction mixture gently shaken under a N2 atmosphere for three hours. The resin was then collected by filtration, and washed consecutively with 5 mL of DMF, 5 mL of methanol, and 5 mL of DCM.

SDMA-cystamide (3): To the modified resin was added 15 mL of 90% trifluoroacetic acid (TFA), the resulting mixture gently shaken for two hours, and filtered. The resin was washed twice with 3 mL of TFA/DCM (1:1 (v/v)). The filtrate and washings were combined and added to 200 mL of cold ether to provide a precipitate. The resulting precipitate was collected by centrifugation and dried under reduced pressure to provide 300 mg of SDMA-cystamide (3). The SDMA-cystamide (3) was characterized by mass spectroscopy. EIS-MS: 262.4 (M+1)+, 132.0 (M+2)+.

SDMA-cystamide hydrochloride salt (4): SDMA-cystamide 3 (300 mg) was reconstituted in 5 ml, of 1.0 N HCl and the resulting mixture was lyophilized to provide a light yellow solid as a foam.

The same general procedure as described above can be used to prepare other SDMA analogs.

Example 2: Conjugation of SDMA Cystamide (3) with Maleimide Activated Protein

A. General procedure for conjugating SDMA cystamide (3) with maleimide activated KLH:
1. Slowly opened a vial of maleimide activated KLH (commercially available from Sigma-Aldrich St. Louis, Mo. (catalog no. K0383)) to release the vacuum.
2. Reconstituted the contents of the vial with 1 mL of water to provide a 5 mg/mL solution of maleimide activated KLH in 20 mM sodium phosphate buffer with 230 mM NaCl, 2 mM EDTA, and 80 mM sucrose, pH 6.6.
3. Prepared a conjugation buffer solution of 20 mM sodium phosphate buffer with 100 mM EDTA and 80 mM sucrose, pH 6.6 by reconstituting conjugation buffer (commercially available from Sigma-Aldrich St. Louis, Mo. (catalog no. C3957)) with 10 mL of water.
4. Dissolved approximately 0.8 mg of hapten (i.e., SDMA cystamide (3)) in 0.5 mL of conjugation buffer. Retained 50 μl of the resulting peptide solution for determination of coupling efficiency (hap-total). The retained hapten solution was stored at 2-8° C.
5. The hapten solution of step 4 was immediately mixed with the maleimide activated KLH solution of step 2 in a reaction vial equipped with stirring bar. The resulting mixture was de-gassed while stirring under a gentle nitrogen stream for about 1-2 minutes.
6. The reaction vial was capped and stirring continued at room temperature for 2 hours or overnight at 2-8° C.
7. 100 μl of the conjugation reaction from step 6 (hap-free) was retained for determination of coupling efficiency.

B: General procedure for conjugating SDMA cystamide (3) with maleimide activated BSA:
1. Slowly opened a vial of maleimide activated BSA (commercially available from Sigma-Aldrich St. Louis, Mo. (catalog no. B7542)) to release the vacuum.
2. Reconstituted the contents of the vial with 1 mL of water to provide a 5 mg/mL solution of maleimide activated BSA in 20 mM sodium phosphate buffer with 230 mM NaCl, 2 mM EDTA, and 80 mM sucrose, pH 6.6.
3. Dissolved 5 mg of hapten (i.e., SDMA cystamide (3)) in 0.5 mL of conjugation buffer (prepared as described above in step A3). Retained 50 μl of the resulting peptide solution for determination of coupling efficiency (hap-total). The retained hapten solution was stored at 2-8° C.
4. The hapten solution of step 3 was immediately mixed with the maleimide activated BSA solution of step 2 in a reaction vial equipped with stirring bar. The resulting mixture was de-gassed while stirring under a gentle nitrogen stream for about 1-2 minutes.
5. The reaction vial was capped and stirring continued at room temperature for 2 hours or overnight at 2-8° C.
6. 100 μl of the conjugation reaction from step 5 (hap-free) was retained for determination of coupling efficiency.

C: Isolation of KLH or BSA conjugates:
1. Dissolved the contents of a phosphate buffered saline package (PBS) package (commercially available from Sigma-Aldrich St. Louis, Mo. (catalog no. P3813)) in 1 liter of water.
2. Supported a Sephadex G-25M gel filtration column (commercially available from Sigma-Aldrich St. Louis, Mo. (catalog no. B4783)) over a beaker.
3. Removed the cap from the top of the column, cut open lower tip of column, and let excess of liquid flow through. Did not allow the column to run dry.
4. Equilibrated the column with 30 mL of PBS.
5. The reaction mixture from Example 2A or 2B was applied to the column.
6. The column was eluted with PBS, using a total volume of about 10 mL and fractions of about 0.5-1.0 mL were collected. The presence of protein in the fractions was monitored by measuring the absorbance of each fraction at 280 nm.
7. The fractions containing protein were combined. FIG. 1 provides a graphical representation of an illustrative elution profile for the proteins KLH (♦) and BSA (■). FIG. 1. graphically depicts absorption v. fraction number.
8. The fractions containing protein were divided into small aliquots that were stored frozen at −20° C.

D. Assay to determine coupling efficiency:
1. Cysteine Standard Assay—To estimate the coupling efficiency of the analog to the cysteine peptide, a standard curve was prepared using known concentrations of cysteine. The assay was based on the reaction of 5,5'-dithiobis(2-nitrobenzoic acid) (DTNB or Ellman's reagent) which reacts with sulfhydryl groups at pH 8.0 to produce a chromophore with maximum absorption at 412 nm. The following procedure was followed:

a. A DTNB buffer was prepared by dissolving the contents of the vial of the DTNB buffer (commercially available from Sigma-Aldrich St. Louis, Mo. (catalog no. D4179) in 10 mL of water.
b. DTNB reagent (commercially available from Sigma-Aldrich St. Louis, Mo. (catalog no. D8130)) was then dissolved in 5 mL of the DTNB buffer from step a.
c. Immediately before use, a cysteine solution was prepared by dissolving 32 mg of L-cysteine hydrochloride monohydrate (commercially available from Sigma-Aldrich St. Louis, Mo. (catalog no. C7880)) in 1 mL of water. The resulting solution of L-cysteine hydrochloride was serially diluted with water to provide diluted stock solutions in the range of 0.4-0.04 mg/mL. The diluted stock solutions were used immediately.
d. To labeled test tubes was added 50 μL of the diluted stock solutions. A test tube containing 50 μL of water was used as a blank.
e. To each test tube was then added 0.1 mL of water, 0.75 mL of DTNB buffer, pH 8.0, and, immediately, 0.1 mL of DTNB reagent solution (1 mg/mL) to provide a final cysteine standard assay solution with a volume of 1 mL.
f. Mixed contents of each test tube.
g. The absorbance of each cysteine standard assay solution was determined at 412 nm. If the absorbance was above 1.4, the samples were diluted and the assay repeated.
h. Absorbance at 412 nm was plotted against cysteine concentration (mg/mL) to provide a standard curve. The linear part of the standard curve, with cysteine concentrations ranging from 2-20 μg/ml, was used for determining hap-total and hap-free.

2. Hapten Assay—Note: If samples generated values higher than the highest cysteine standard in the cysteine standard assay, the samples were diluted and the assay repeated.

a. To appropriately labeled test tubes was added 50 μl of the following solutions to:
  (i) DTNB Buffer (Blank)
  (ii) Diluted peptide sample (hap-total, from KLH conjugation, from step A4 of Example 2)
  (iii) hapten-KLH (hap-free, from KLH conjugation step A7 of Example 2)
  (iv) Diluted peptide sample (hap-total, from BSA conjugation step B3 of Example 2)
  (v) hap-BSA (hap-free, from BSA conjugation, step B6 of Example 2)
b. To each labeled tube from step (a) was added 0.1 mL of water, 0.75 mL of DTNB buffer, pH 8.0, and, immediately, 0.1 ml of DTNB reagent solution (1 mg/mL), to provide a final hapten assay solution with a volume of 1 mL.
c. Mixed the contents of each tube.
d. The absorbance of the solution in each labeled tube was determined at 412 nm. If the absorbance was above 1.4, the samples are diluted and the assay repeated.
e. The concentration of hap-total was then determined from the measured absorbance using the standard curve obtained as described above in section 1 h. The absorbance measured for tube (ii) and tube (iv) were used to determine hap-total for KLH and BSA, respectively. The absorbance measured for tube (iii) and tube (v) were used to determine hap-free for KLH and BSA, respectively. The peptide concentration in the undiluted solution and coupling efficiency were then calculated as described under calculations.

3. Calculations

To estimate the peptide concentrations and coupling efficiency, a standard curve was prepared using known concentrations of cysteine as described above (Cysteine Standard Assay). In this calculation, one mole of cysteine is equivalent to one mole of sulfhydryl containing hapten.

The following formulas were used:

% Coupling Efficiency={($Hap$(conjugated)/$Hap$(total)}×100=[{$Hap$(total)−$Hap$(free)}/$Hap$(total)]×100

$Hap$(total)=Peptide(total)μmole/ml $Hap$(free)=Peptide(free)μmole/ml $Hap$(conjugated)=$Hap$(total)−$Hap$(free)

(See, also, Sigma-Aldrich Technical Bulletin for Maleimide Activated BSA, KLH Conjugation Kit (catalog no. MBK1)). This same general procedure as described in Examples 2A-D can be used to measure the efficiency of the conjugation of other SDMA analogs to KLH and BSA.

Example 3: Method for Generating Anti-SDMA Antibodies

The immunization protocol for generating the anti-SDMA antibodies of the invention was carried out as follows:

Six California breed rabbits were immunized with an SDMA-conjugate of the invention. Three of the six rabbits were immunized with SDMA conjugated with BSA (rabbits #155, 156 and 157) and the other three rabbits were immunized with SDMA conjugated with KLH (rabbits #152, 153 and 154) (prepared as described in Example 2). For primary immunizations, each rabbit was injected with 0.5 mg of the SDMA conjugate in 1 ml of phosphate buffered saline (PBS) mixed with 1 ml of Freund's complete adjuvant. Each rabbit received 20-30 intradermal injections on their shaved back. Each rabbit was boosted with 0.25 mg of immunogen in 1 ml PBS mixed with equal volume of Freund's incomplete adjuvant in the hind legs. The boosting shots were given each month after the primary injection. Test bleeds of 5 ml blood were taken from each rabbit 7-10 days after each boost. Production bleeds of 40 ml were taken from each rabbit after the third booster shot, when the antisera titer was greater than about 1:2000. Antiserum titer is the dilution of antiserum that generates the steepest calibration curve for the assay.

Example 4: Characterization of Anti-SDMA Antibodies

In order to assess the specificity of the antibodies obtained by the procedures described in Example 3 above, their reactivity to SDMA, ADMA, L-arginine, and/or N-methyl-arginine was measured in a competitive ELISA assay (Table 1).

ADMA-2HCl, SDMA-2HCl, N-methylarginine acetate (Sigma, Cat. No. M7033) or L-arginine (Sigma, Cat. No. A5006) were each dissolved in PBS to make stock solutions at 1 mg/ml. From these stock solutions, working solutions at 100 μg/ml, 10 μg/m and 1 μg/m were prepared in PBS.

50 µl of the SDMA-HRP conjugate (as described in Example 5 below), 50 µl of ADMA, SDMA, N-methylarginine or L-arginine (at concentrations from 1-100 µg/ml as described above), and 50 µl of rabbit anti-SDMA antibody in serum (1:3000 titer) were sequentially added to an individual well in a 96-well polystyrene microwell plate, precoated with sheep anti-rabbit IgG (commercially available from Beacon Analytical Systems Inc. of Portland, Me.). After a 30 minutes incubation period at room temperature, the wells were washed 4 times with PBST (Phosphate Buffered Saline, 0.05% Tween).

100 µl of 3,3',5,5'-Tetramethylbenzidine (commercially available from Promega Corporation of Madison, Wis.) was subsequently added. Following a 30 minutes incubation period at room temperature, 100 µl of stop solution (1 N HCl) was added and the absorbance was measured at 450 nm using a BioTek ELX 808 (Winooski, Vt.) plate reader. The data was subjected to quantification using Softmax software (Molecular Devices, Sunnyvale, Calif.).

The absorbance values obtained with 0 µg/mL, 1 µg/mL, 10 µg/mL, and 100 µg/mL of ADMA, SDMA, N-methylarginine or L-arginine, respectively, were determined and plotted. The concentration of SDMA at which the absorbance value was reduced by 50% (relative to the maximum absorbance obtained at 0 µg/mL SDMA; i.e. IC50) was divided by each of the concentrations of ADMA, N-methylarginine or L-arginine, respectively, at which the absorbance value was reduced by 50% (IC50). The resulting value was multiplied by 100 to obtain the value "% cross-reactivity". Where an absorbance reduction of <50% was observed at concentrations up to and including 100 µg/mL, a cross-reactivity of <1% was noted (See Table 1).

As shown in Table 1, all 6 rabbit anti-SDMA sera had cross-reactivities of <1% to ADMA, N-methylarginine or L-arginine, respectively.

TABLE 1

| | IC 50 | % Cross Reactivity |
|---|---|---|
| Rabbit # 152 (1: 5K) | | |
| SDMA | 1.10 ug/ml | 100% |
| ADMA | >100 | <1% |
| L-Arginine | >100 | <1% |
| N-MMA | >100 | <1% |
| Rabbit # 153 (1: 2.5K) | | |
| SDMA | 0.65 ug/ml | 100% |
| ADMA | >100 | <1% |
| L-Arginine | >100 | <1% |
| N-MMA | >100 | <1% |
| Rabbit # 154 (1.25K) | | |
| SDMA | 0.49 ug/ml | 100% |
| ADMA | >100 | <1% |
| L-Arginine | >100 | <1% |
| N-MMA | >100 | <1% |
| Rabbit # 155 (1: 3K) | | |
| SDMA | 0.73 ug/ml | 100% |
| ADMA | >100 | <1% |
| L-Arginine | >100 | <1% |
| N-MMA | 79 ug/ml | <1% |
| Rabbit # 156 (1: 20K) | | |
| SDMA | 1.3 ug/ml | 100% |
| ADMA | >100 | <1% |
| L-Arginine | >100 | <1% |
| N-MMA | >100 | <1% |

TABLE 1-continued

| | IC 50 | % Cross Reactivity |
|---|---|---|
| Rabbit # 157 (1: 15K) | | |
| SDMA | 1.6 ug/ml | 100% |
| ADMA | >100 | <1% |
| L-Arginine | >100 | <1% |
| N-MMA | >100 | <1% |

A similar experiment to that described in Examples 1-4, but wherein ADMA was used rather than SDMA, also generated antibodies. Using an ADMA-protein conjugate to generate antibodies, however, produced antibodies that were not specific to free ADMA and were not useful in an assay to measure ADMA.

In another experiment, using only polyclonal antibody from Rabbit No. 154, the specificity of the antibody was determined with greater stringency by the method described above. This data shows that that the specificity for antibody from Rabbit No. 154 is even greater than shown in Table 1, above.

| Specificity (Cross-Reactivity) Rabbit No. 154 | |
|---|---|
| | Cross-reactivity |
| SDMA | 100% |
| ADMA | <0.2% |
| Arginine | <0.01% |
| LMMA | <1% |

Example 5: Competitive Immunoassay for Detecting In Vivo SDMA Levels

Serum samples were provided by veterinary clinics/labs from animals that were subjected to a routine physical exam and a routine chemistry panel.

A SDMA-HRP conjugate was prepared according to the following procedure:
1. Maleimide activated horseradish peroxidase lyophilized powder, >200 units/mg protein (commercially available from Sigma-Aldrich St. Louis, Mo. Product no. P1709)) was reconstituted to 2-5 mg/mL in 0.15 M NaCl, 0.1 M sodium phosphate, pH 7.0. The buffer was deaerated and purged with nitrogen or argon before use and the water used to prepare the buffer was free of trace heavy metals and other oxidizing agents. The coupling was performed in an amber vial to protect the reaction from light.
2. SDMA analog (3) was dissolved in the same buffer as used in step 1 to provide a solution with a concentration of 2-5 mg/mL. Generally 1-2-moles of peroxidase per mole sulfhydryl compound was used. The molecular weight of peroxidase is about 40,000.
3. The solution from step 1 was combined with the solution from step 2 and the resulting solution stirred gently for 3 hours at room temperature. Unreacted maleimide groups were then blocked by adding 1M 2-Mercaptoethanol (commercially available from Sigma-Aldrich St. Louis, Mo. (catalog no. M 6250)) to provide a final concentration of 0.0015 M 2-Mercaptoethanol and the resulting solution is stirred for about 15 minutes.
4. Unreacted sulfhydryl groups were then blocked by adding 0.3 M N-ethylmaleimide (commercially available from Sigma-Aldrich St. Louis, Mo. (catalog no. D 8654)) to the solution from step 3 to provide a final concentration of 0.003 M N-ethylmaleimide.

5. The resulting solution of the SDMA-HRP conjugate was then exchanged into PBS by chromatography (using the same procedure described above in the Example for conjugating SDMA analog (3) to maleimide activated KLH and BSA) or dialysis into PBS (Spectra/Por3, MWCO 3500 Spectrum Labs, Rancho Dominguez, Calif.) according to the instructions from the manufacturer. The resulting solution was then lyophilized.

See, also, Lin, F. T., et al., Biochemistry, 18(4), 690 (1979); Kitagawa, T., et al., Chem. Pharm. Bull., 29(4), 1131 (1981); Duncan, R. J. S., et al., Anal. Biochem., 132, 68 (1983); and Palmer, J. L., et al., J. Biol. Chem., 238(7), 2393 (1963).

50 µl of the SDMA-HRP conjugate, 50 µl of serum sample (or calibrator, SDMA 2 HCl, commercially available from Calbiochem of San Diego, Calif.), and 50 µl of rabbit anti-SDMA antibody in serum (1:3000 titer) were sequentially added to an individual well in a 96-well polystyrene microwell plate, precoated with sheep anti-rabbit IgG (commercially available from Beacon Analytical Systems Inc. of Portland, Me.). After a 30 minutes incubation period at room temperature, the wells were washed 4 times with PBST (Phosphate Buffered Saline, 0.05% Tween).

100 µl of 3,3',5,5'-Tetramethylbenzidine (commercially available from Promega Corporation of Madison, Wis.) was subsequently added. Following a 30 minutes incubation period at room temperature, 100 µl of stop solution (1 N HCl) was added and the absorbance was measured at 450 nm using a BioTek ELX 808 (Winooski, Vt.) plate reader. The data was subjected to quantification using Softmax software (Molecular Devices, Sunnyvale, Calif.). A calibration curve was generated by running a series of SDMA standards (e.g., 0, 0.05 µg/mL, 0.15 µg/mL, 0.45 µg/mL, and 1.35 µg/mL). The unknown samples were quantified using the calibration curve. The results are summarized in Table 2.

TABLE 2

| Species | Status | SDMA µM |
|---|---|---|
| Canine | Healthy | 1.1 |
| Canine | Healthy | 1.1 |
| Canine | Healthy | 1.1 |
| Canine | Healthy | 0.7 |
| Canine | Healthy | 1.7 |
| Canine | Healthy | 1.4 |
| Canine | Healthy | 1.2 |
| Canine | Healthy | 1.7 |
| Canine | Healthy | 1.9 |
| Canine | Renal Disease | 13.3 |
| Canine | Renal Disease | 6.1 |
| Canine | Renal Disease | 2.8 |
| Canine | Renal Disease | 2.2 |
| Canine | Renal Disease | 3.5 |
| Canine | Renal Disease | 2.3 |
| Canine | Renal Disease | 1.8 |
| Feline | Healthy | 2.7 |
| Feline | Healthy | 2.9 |
| Feline | Healthy | 3.0 |
| Feline | Healthy | 2.7 |
| Feline | Healthy | 2.5 |
| Feline | Healthy | 2.2 |
| Feline | Healthy | 2.1 |
| Feline | Healthy | 1.9 |
| Feline | Renal Disease | 70.3 |
| Feline | Renal Disease | 6.0 |
| Feline | Renal Disease | 5.2 |
| Feline | Renal Disease | 3.9 |

In Table 2, the status "Renal Disease" indicates that the sample taken from the animal showed creatinine and blood urea nitrogen (BUN) values above the normal reference range and the status "Healthy" indicates that the sample taken from the animal showed normal (reference range) creatinine and blood urea nitrogen (BUN) values. For canines, the upper limit of the normal reference range was 27 mg/dL for BUN and 1.8 mg/dL for creatinine. For felines, the upper limit of the normal reference range was 34 mg/dL for BUN, and 2.3 mg/dL for creatinine.

The results in Table 2 show that SDMA levels were elevated in dogs and cats with compromised kidney function. Thus, SDMA can be used as a marker to diagnose renal disease in animals.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in molecular biology, immunology, chemistry, biochemistry or in the relevant fields are intended to be within the scope of the appended claims.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that, as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the invention. The disclosures of all references and publications cited above are expressly incorporated by reference in their entireties to the same extent as if each were incorporated by reference individually.

What is claimed is:

1. A compound having the structure:

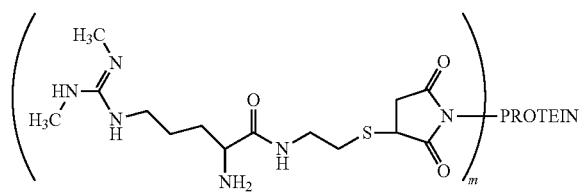

wherein protein is a protein and m is an integer of 5 or greater.

2. The compound of claim 1, wherein the protein is selected from the group consisting of keyhole limpet protein (KLH), bovine serum albumin (BSA), and ovalbumin.

3. The compound of claim 2, wherein the protein is KLH.

4. The compound of claim 2, wherein the protein is BSA.

5. The compound of claim 1, wherein the protein is an enzyme.

6. The compound of claim 5, wherein the enzyme is horseradish peroxidase (HRP).

7. A polyclonal anti-SDMA antibody, wherein the antibody has cross reactivity of less than 1% for each of asymmetrical dimethylarginine (AMDA), L-arginine and N-methylarginine compared to 100% cross reactivity for symmetrical dimethylarginine (SDMA), wherein said cross-reactivity is measured in the presence of the compound of claim 6.

8. A complex comprising a compound of the formula:

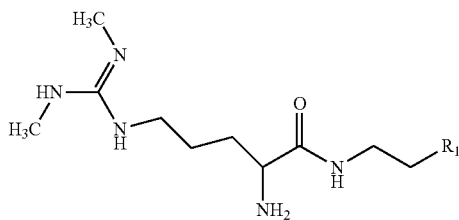

or a salt thereof, wherein $R_1$ is X—$R_2$ and X is O or S and $R_2$ is a label having a thiol or hydroxyl reactive group, wherein the compound is bound to an antibody that specifically binds free symmetrical dimethylarginine (SDMA), wherein the antibody has reactivity for asymmetrical dimethylarginine (ADMA) of less than 10% of its reactivity for SDMA.

9. The complex of claim 8, wherein the label is selected from the group consisting of radioisotope labels, chemiluminescent dyes, electrochemical labels, metal chelates, latex particles, fluorescent labels, enzymatic labels, horseradish peroxidase, alkaline phosphatase, biotin, avidin, streptavidin, digioxigenin, maltose, oligohistidine, 2, 4-dinitrobenzene, phenylarsenate, ssDNA, and dsDNA.

10. The complex of claim 8, wherein the label is a protein.

11. The complex of claim 10, wherein the protein is an enzyme.

12. The complex of claim 8, wherein the antibody has reactivity for asymmetrical dimethylarginine (ADMA) of less than 5% of its reactivity for SDMA.

13. The complex of claim 8, wherein the antibody has reactivity for asymmetrical dimethylarginine (ADMA) of less than 1% of its reactivity for SDMA.

14. A complex comprising a compound of the formula:

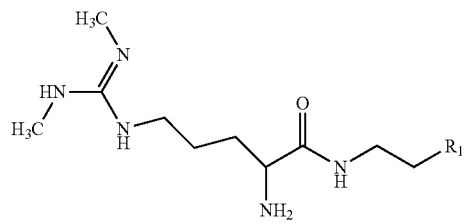

or a salt thereof, wherein $R_1$ is X—$R_2$, wherein X is O or S and $R_2$ is a protein functionalized with a thiol or hydroxyl reactive group, wherein the compound is bound to an antibody that specifically binds free symmetrical dimethylarginine (SDMA) and that has no or substantially no cross reactivity with one or more compounds selected from the group consisting of asymmetrical dimethylarginine (ADMA), L-arginine, and N-methylarginine.

15. The complex of claim 14, wherein the protein is maleimide activated.

16. The complex of claim 14, wherein the protein is an enzyme.

17. The complex of claim 14, wherein the antibody has reactivity for asymmetrical dimethylarginine (ADMA) of less than 25% of its reactivity for SDMA.

18. The complex of claim 14, wherein the antibody has reactivity for asymmetrical dimethylarginine (ADMA) of less than 10% of its reactivity for SDMA.

19. The complex of claim 14, wherein the antibody has reactivity for asymmetrical dimethylarginine (ADMA) of less than 5% of its reactivity for SDMA.

20. The complex of claim 14, wherein the antibody has reactivity for asymmetrical dimethylarginine (ADMA) of less than 1% of its reactivity for SDMA.

21. A complex comprising the compound of claim 1 bound to an antibody that specifically binds free symmetrical dimethylarginine (SDMA).

22. The complex of claim 21, wherein the antibody has no or substantially no cross reactivity with one or more compounds selected from the group consisting of asymmetrical dimethylarginine (ADMA), L-arginine, and N-methylarginine.

23. The complex of claim 21, wherein the antibody has reactivity for asymmetrical dimethylarginine (ADMA) of less than 25% of its reactivity for SDMA.

24. The complex of claim 21, wherein the antibody has reactivity for asymmetrical dimethylarginine (ADMA) of less than 10% of its reactivity for SDMA.

25. The complex of claim 21, wherein the antibody has reactivity for asymmetrical dimethylarginine (ADMA) of less than 5% of its reactivity for SDMA.

26. The complex of claim 21, wherein the antibody has reactivity for asymmetrical dimethylarginine (ADMA) of less than 1% of its reactivity for SDMA.

27. A kit for determining the presence of free symmetrical dimethylarginine (SDMA) in a sample, the kit comprising (a) a compound of the formula:

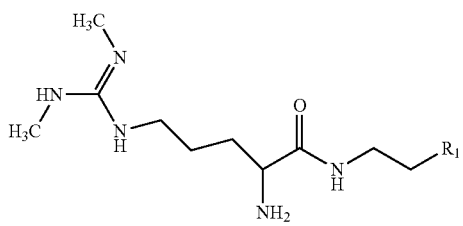

or a salt thereof, wherein $R_1$ is X—$R_2$ and X is O or S and $R_2$ is a label having a thiol or hydroxyl reactive group, and (b) an antibody that specifically binds free SDMA and that has no or substantially no cross reactivity with one or more compounds selected from the group consisting of asymmetrical dimethylarginine (ADMA), L-arginine, and N-methylarginine.

28. The kit of claim 27, wherein the antibody has reactivity for asymmetrical dimethylarginine (ADMA) of less than 25% of its reactivity for SDMA.

29. The kit of claim 27, wherein the antibody has reactivity for asymmetrical dimethylarginine (ADMA) of less than 10% of its reactivity for SDMA.

30. The kit of claim 27, wherein the antibody has reactivity for asymmetrical dimethylarginine (ADMA) of less than 5% of its reactivity for SDMA.

31. The kit of claim 27, wherein the antibody has reactivity for asymmetrical dimethylarginine (ADMA) of less than 1% of its reactivity for SDMA.

32. A kit for determining the presence of free symmetrical dimethylarginine (SDMA) in a sample, the kit comprising (a) a compound of the formula:

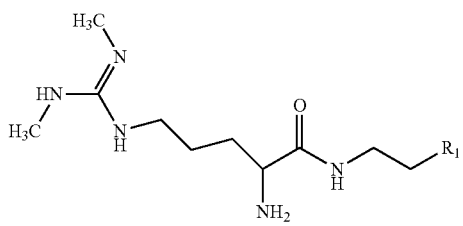

or a salt thereof, wherein $R_1$ is X—$R_2$, wherein X is O or S and $R_2$ is a protein functionalized with a thiol or hydroxyl reactive group, and (b) an antibody that specifically binds free SDMA and that has no or substantially no cross reactivity with one or more compounds selected from the group consisting of asymmetrical dimethylarginine (ADMA), L-arginine, and N-methylarginine.

33. The kit of claim 32, wherein the antibody has reactivity for asymmetrical dimethylarginine (ADMA) of less than 25% of its reactivity for SDMA.

34. The kit of claim 32, wherein the antibody has reactivity for asymmetrical dimethylarginine (ADMA) of less than 10% of its reactivity for SDMA.

35. The kit of claim 32, wherein the antibody has reactivity for asymmetrical dimethylarginine (ADMA) of less than 5% of its reactivity for SDMA.

36. The kit of claim 32, wherein the antibody has reactivity for asymmetrical dimethylarginine (ADMA) of less than 1% of its reactivity for SDMA.

37. A kit for determining the presence of free symmetrical dimethylarginine (SDMA) in a sample, the kit comprising the compound of claim 1.

38. The kit of claim 37, further comprising an antibody that specifically binds free SDMA.

39. The kit of claim 38, wherein the antibody has no or substantially no cross reactivity with one or more compounds selected from the group consisting of asymmetrical dimethylarginine (ADMA), L-arginine, and N-methylarginine.

40. The kit of claim 38, wherein the antibody has reactivity for asymmetrical dimethylarginine (ADMA) of less than 25% of its reactivity for SDMA.

41. The kit of claim 38, wherein the antibody has reactivity for asymmetrical dimethylarginine (ADMA) of less than 10% of its reactivity for SDMA.

42. The kit of claim 38, wherein the antibody has reactivity for asymmetrical dimethylarginine (ADMA) of less than 5% of its reactivity for SDMA.

43. The kit of claim 38, wherein the antibody has reactivity for asymmetrical dimethylarginine (ADMA) of less than 1% of its reactivity for SDMA.

44. A method for detecting the presence or amount of free symmetrical dimethylarginine (SDMA) in a sample, the method comprising:
(a) contacting the sample with (i) a compound of the formula

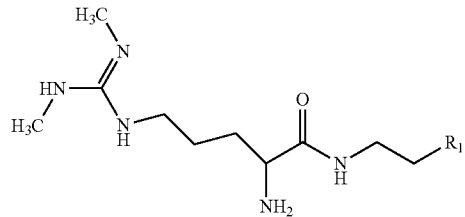

or a salt thereof, wherein $R_1$ is X—$R_2$ and X is O or S and $R_2$ is a label having a thiol or hydroxyl reactive group, and (ii) an antibody that specifically binds free SDMA and that has no or substantially no cross reactivity with one or more compounds selected from the group consisting of asymmetrical dimethylarginine (ADMA), L-arginine, and N-methylarginine, and
(b) detecting the presence or amount of the label associated with the antibody, thereby determining the presence or amount of free SDMA in the sample.

45. The method of claim 44, wherein the antibody has reactivity for asymmetrical dimethylarginine (ADMA) of less than 25% of its reactivity for SDMA.

46. The method of claim 44, wherein the antibody has reactivity for asymmetrical dimethylarginine (ADMA) of less than 10% of its reactivity for SDMA.

47. The method of claim 44, wherein the antibody has reactivity for asymmetrical dimethylarginine (ADMA) of less than 5% of its reactivity for SDMA.

48. The method of claim 44, wherein the antibody has reactivity for asymmetrical dimethylarginine (ADMA) of less than 1% of its reactivity for SDMA.

49. A method for detecting the presence or amount of free symmetrical dimethylarginine (SDMA) in a sample, the method comprising:

(a) contacting the sample with (i) a compound of the formula:

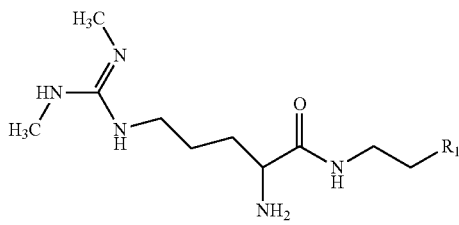

or a salt thereof, wherein $R_1$ is $X—R_2$, wherein X is O or S and $R_2$ is an enzyme functionalized with a thiol or hydroxyl reactive group, and (ii) an antibody that specifically binds free SDMA and that has no or substantially no cross reactivity with one or more compounds selected from the group consisting of asymmetrical dimethylarginine (ADMA), L-arginine, and N-methylarginine, and (b) detecting the presence or amount of the enzyme associated with the antibody, thereby determining the presence or amount of free SDMA in the sample.

50. The method of claim 49, wherein the antibody has reactivity for asymmetrical dimethylarginine (ADMA) of less than 25% of its reactivity for SDMA.

51. The method of claim 49, wherein the antibody has reactivity for asymmetrical dimethylarginine (ADMA) of less than 10% of its reactivity for SDMA.

52. The method of claim 49, wherein the antibody has reactivity for asymmetrical dimethylarginine (ADMA) of less than 5% of its reactivity for SDMA.

53. The method of claim 49, wherein the antibody has reactivity for asymmetrical dimethylarginine (ADMA) of less than 1% of its reactivity for SDMA.

54. A method for detecting the presence or amount of free symmetrical dimethylarginine (SDMA) in a sample, the method comprising:
(a) contacting the sample with compound of claim 5 and an antibody that specifically binds free SDMA, and
(b) detecting the presence or amount of the enzyme associated with the antibody, thereby determining the presence or amount of free SDMA in the sample.

55. The method of claim 54, wherein the antibody has reactivity for asymmetrical dimethylarginine (ADMA) of less than 25% of its reactivity for SDMA.

56. The method of claim 54, wherein the antibody has reactivity for asymmetrical dimethylarginine (ADMA) of less than 10% of its reactivity for SDMA.

57. The method of claim 54, wherein the antibody has reactivity for asymmetrical dimethylarginine (ADMA) of less than 5% of its reactivity for SDMA.

58. The method of claim 54, wherein the antibody has reactivity for asymmetrical dimethylarginine (ADMA) of less than 1% of its reactivity for SDMA.

59. A device for determining the presence of free symmetrical dimethylarginine (SDMA) in a sample, the device comprising a solid phase having immobilized thereon (a) an antibody that specifically binds free SDMA and that has no or substantially no cross reactivity with one or more compounds selected from the group consisting of asymmetrical dimethylarginine (ADMA), L-arginine, and N-methylarginine, and (b) a compound of the formula:

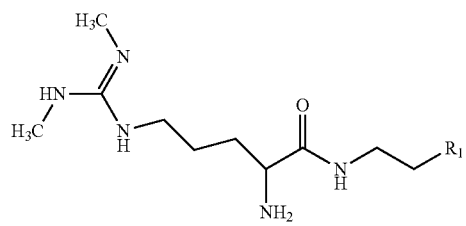

or a salt thereof, wherein $R_1$ is $X—R_2$ and X is O or S and $R_2$ is a label having a thiol or hydroxyl reactive group, wherein the compound is bound to the antibody.

60. The device of claim 28, wherein the antibody has reactivity for asymmetrical dimethylarginine (ADMA) of less than 25% of its reactivity for SDMA.

61. The device of claim 28, wherein the antibody has reactivity for asymmetrical dimethylarginine (ADMA) of less than 10% of its reactivity for SDMA.

62. The device of claim 28, wherein the antibody has reactivity for asymmetrical dimethylarginine (ADMA) of less than 5% of its reactivity for SDMA.

63. The device of claim 28, wherein the antibody has reactivity for asymmetrical dimethylarginine (ADMA) of less than 1% of its reactivity for SDMA.

64. A device for determining the presence of free symmetrical dimethylarginine (SDMA) in a sample, the device comprising a solid phase having immobilized thereon (a) an antibody that specifically binds free SDMA and that has no or substantially no cross reactivity with one or more compounds selected from the group consisting of asymmetrical dimethylarginine (ADMA), L-arginine, and N-methylarginine, and (b) a compound of the formula:

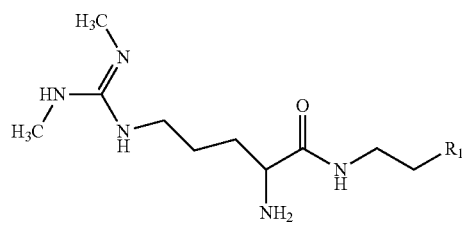

or a salt thereof, wherein $R_1$ is $X—R_2$, wherein X is O or S and $R_2$ is a protein functionalized with a thiol or hydroxyl reactive group, wherein the compound is bound to the antibody.

65. The device of claim 30, wherein the antibody has reactivity for asymmetrical dimethylarginine (ADMA) of less than 25% of its reactivity for SDMA.

66. The device of claim 30, wherein the antibody has reactivity for asymmetrical dimethylarginine (ADMA) of less than 10% of its reactivity for SDMA.

67. The device of claim 30, wherein the antibody has reactivity for asymmetrical dimethylarginine (ADMA) of less than 5% of its reactivity for SDMA.

68. The device of claim 30, wherein the antibody has reactivity for asymmetrical dimethylarginine (ADMA) of less than 1% of its reactivity for SDMA.

69. A device for determining the presence of free symmetrical dimethylarginine (SDMA) in a sample, the device comprising a solid phase having immobilized thereon the compound of claim 5.

70. The device of claim 69, wherein the compound is bound to an antibody specific for free Symmetrical Dimethylarginine (SDMA).

71. The device of claim 70, wherein the antibody has no or substantially no cross reactivity with one or more compounds selected from the group consisting of asymmetrical dimethylarginine (ADMA), L-arginine, and N-methylarginine.

72. The device of claim 70, wherein the antibody has reactivity for asymmetrical dimethylarginine (ADMA) of less than 25% of its reactivity for SDMA.

73. The device of claim 70, wherein the antibody has reactivity for asymmetrical dimethylarginine (ADMA) of less than 10% of its reactivity for SDMA.

74. The device of claim 70, wherein the antibody has reactivity for asymmetrical dimethylarginine (ADMA) of less than 5% of its reactivity for SDMA.

75. The device of claim 70, wherein the antibody has reactivity for asymmetrical dimethylarginine (ADMA) of less than 1% of its reactivity for SDMA.

* * * * *